United States Patent [19]
Laufer et al.

[11] Patent Number: 6,033,397
[45] Date of Patent: Mar. 7, 2000

[54] METHOD AND APPARATUS FOR TREATING ESOPHAGEAL VARICES

[75] Inventors: Michael D. Laufer, Menlo Park; Brian E. Farley, Los Altos, both of Calif.

[73] Assignee: Vnus Medical Technologies, Inc., Sunnyvale, Calif.

[21] Appl. No.: 08/717,994

[22] Filed: Sep. 26, 1996

Related U.S. Application Data

[63] Continuation-in-part of application No. 08/610,911, Mar. 5, 1996.

[51] Int. Cl.⁷ .................................................... A61B 17/38
[52] U.S. Cl. ................................ 606/27; 606/28; 606/32; 606/50; 606/31; 604/20; 604/105; 604/113
[58] Field of Search ...................................... 128/642, 644, 128/637–641, 653.4, 656, 658, 898; 604/19–21, 48–50, 53, 54, 93, 96, 102, 104, 105–107, 113, 114, 264, 280, 523; 606/27, 28, 32, 33, 48–51, 31, 191, 192, 194; 600/373, 435, 433

[56] References Cited

U.S. PATENT DOCUMENTS

| | | |
|---|---|---|
| 373,399 | 11/1887 | Hamilton . |
| 659,409 | 10/1900 | Mosher . |
| 833,759 | 10/1906 | Sourwine . |
| 985,865 | 3/1911 | Turner, Jr. . |
| 3,230,957 | 1/1966 | Seifert . |

(List continued on next page.)

FOREIGN PATENT DOCUMENTS

| | | |
|---|---|---|
| 0 189 329 | 7/1986 | European Pat. Off. . |
| 0 205 851 | 12/1986 | European Pat. Off. . |
| 0 472 368 A2 | 2/1992 | European Pat. Off. . |
| 0 629 382 A1 | 12/1994 | European Pat. Off. ........ A61B 17/36 |
| 0 738 501 A1 | 10/1996 | European Pat. Off. ........ A61B 17/28 |
| 3516830 | 11/1986 | Germany . |
| WO 90/07303 | 7/1990 | WIPO . |
| WO 92/12681 | 8/1992 | WIPO . |
| WO 93/21846 | 11/1993 | WIPO ............................ A61B 17/39 |
| WO 94/07446 | 4/1994 | WIPO . |
| WO 94/21170 | 9/1994 | WIPO ............................. A61B 5/04 |
| WO 95/02370 | 1/1995 | WIPO . |
| WO 95/10236 | 4/1995 | WIPO ............................ A61B 17/39 |
| WO 95/10322 | 4/1995 | WIPO . |
| WO 95/10978 | 4/1995 | WIPO . |
| WO 95/31142 | 11/1995 | WIPO ............................ A61B 17/20 |
| WO 96/32885 | 10/1996 | WIPO ............................. A61B 5/04 |
| WO 97/17892 | 5/1997 | WIPO ............................. A61B 5/04 |

OTHER PUBLICATIONS

Don Crockett, Jr., M.D., et al., Preliminary Experience with an Endovascular Catheter for Electrocoagulation of Peripheral Veins, The Journal of Vascular Technology, Winter 1996, at 19–22.

Samuel R. Money, M.D., Endovascular Elecrtroablation of Peripheral Veins, 22 Annual Symposium, Current Critical Problems, New Horizons and Techniques in Vascular and Endovascular Surgery (Nov. 1995).

(List continued on next page.)

*Primary Examiner*—Corrine McDermott
*Assistant Examiner*—Cris L. Rodriguez
*Attorney, Agent, or Firm*—Fulwilder Patton Lee & Utecht, LLP

[57] ABSTRACT

A catheter delivers an electrode within a vein for a minimally invasive treatment of esophageal varices using RF energy. The catheter is introduced into and positioned within the section of the vein to be treated. The electrode radiates high frequency energy towards the vein, and the surrounding venous tissue becomes heated and begins to shrink. The extent of shrinkage of the vein is detected by fluoroscopy. The electrode remains active until there has been sufficient shrinkage of the vein. The electrode may remain active for an extended period of time so as to promote a thickening of the immediately surrounding esophageal tissue. The catheter includes a controllable member for limiting the amount of shrinkage of the vein to the diameter of the member. After treating one section of the vein, the catheter and the electrode are repositioned within the venous system to treat different sections until all desired venous sections are rendered functionally competent.

41 Claims, 10 Drawing Sheets

U.S. PATENT DOCUMENTS

| | | | |
|---|---|---|---|
| 3,301,258 | 1/1967 | Werner et al. . | |
| 3,557,794 | 1/1971 | Van Patten . | |
| 3,920,021 | 11/1975 | Hiltebrandt . | |
| 4,016,886 | 4/1977 | Doss et al. . | |
| 4,043,338 | 8/1977 | Homm et al. . | |
| 4,119,102 | 10/1978 | LeVeen . | |
| 4,154,246 | 5/1979 | LeVeen . | |
| 4,312,364 | 1/1982 | Convert et al. . | |
| 4,346,715 | 8/1982 | Gammell . | |
| 4,464,175 | 8/1984 | Altman et al. | 604/99 |
| 4,512,338 | 4/1985 | Balko et al. | 128/1 R |
| 4,522,205 | 6/1985 | Taylor et al. . | |
| 4,643,186 | 2/1987 | Rosen et al. . | |
| 4,658,836 | 4/1987 | Turner . | |
| 4,660,571 | 4/1987 | Hess et al. . | |
| 4,664,120 | 5/1987 | Hess . | |
| 4,699,147 | 10/1987 | Chilson et al. . | |
| 4,709,698 | 12/1987 | Johnston et al. | 128/303.12 |
| 4,765,331 | 8/1988 | Petruzzi et al. . | |
| 4,776,349 | 10/1988 | Nashef et al. . | |
| 4,807,620 | 2/1989 | Strul et al. . | |
| 4,823,812 | 4/1989 | Eshel et al. . | |
| 4,945,912 | 8/1990 | Langberg . | |
| 4,966,597 | 10/1990 | Cosman . | |
| 4,976,711 | 12/1990 | Parins et al. . | |
| 4,979,948 | 12/1990 | Geddes et al. . | |
| 5,010,894 | 4/1991 | Edhag . | |
| 5,035,694 | 7/1991 | Kasprzyk . | |
| 5,047,028 | 9/1991 | Qian | 606/49 |
| 5,057,106 | 10/1991 | Kasevich et al. . | |
| 5,057,107 | 10/1991 | Parins et al. . | |
| 5,078,717 | 1/1992 | Parins et al. . | |
| 5,098,429 | 3/1992 | Sterzer . | |
| 5,098,431 | 3/1992 | Rydell . | |
| 5,117,828 | 6/1992 | Metzger et al. . | |
| 5,122,137 | 6/1992 | Lennox . | |
| 5,156,151 | 10/1992 | Imran . | |
| 5,188,602 | 2/1993 | Nichols . | |
| 5,190,517 | 3/1993 | Zieve et al. . | |
| 5,215,103 | 6/1993 | Desai . | |
| 5,255,678 | 10/1993 | Deslauriers et al. . | |
| 5,263,493 | 11/1993 | Avitall . | |
| 5,275,610 | 1/1994 | Eberbach . | |
| 5,281,218 | 1/1994 | Imran . | |
| 5,293,869 | 3/1994 | Edwards et al. . | |
| 5,314,466 | 5/1994 | Stern et al. . | |
| 5,370,677 | 12/1994 | Rudie et al. . | |
| 5,370,678 | 12/1994 | Edwards et al. . | |
| 5,383,917 | 1/1995 | Desai et al. . | |
| 5,397,339 | 3/1995 | Desai . | |
| 5,403,312 | 4/1995 | Yates . | |
| 5,405,322 | 4/1995 | Lennox et al. . | |
| 5,405,346 | 4/1995 | Grundy et al. . | |
| 5,409,000 | 4/1995 | Imran . | |
| 5,411,025 | 5/1995 | Webster, Jr. . | |
| 5,423,815 | 6/1995 | Fugo . | |
| 5,431,649 | 7/1995 | Mulier et al. . | |
| 5,437,664 | 8/1995 | Cohen et al. . | |
| 5,447,529 | 9/1995 | Marchlinski et al. . | |
| 5,449,381 | 9/1995 | Imran . | |
| 5,454,809 | 10/1995 | Janssen . | |
| 5,458,596 | 10/1995 | Lax et al. . | |
| 5,462,545 | 10/1995 | Wang et al. . | |
| 5,465,717 | 11/1995 | Imran et al. . | |
| 5,470,309 | 11/1995 | Edwards et al. | 604/22 |
| 5,472,441 | 12/1995 | Edwards et al. | 606/41 |
| 5,505,730 | 4/1996 | Edwards . | |
| 5,514,130 | 5/1996 | Baker . | |
| 5,545,161 | 8/1996 | Imran . | |
| 5,556,396 | 9/1996 | Cohen et al. . | |
| 5,626,578 | 5/1997 | Tihon . | |
| 5,643,257 | 7/1997 | Cohen et al. | 606/48 |
| 5,653,240 | 8/1997 | Zimmon | 128/673 |
| 5,709,224 | 1/1998 | Behl et al. | 128/898 |
| 5,810,804 | 9/1998 | Gough et al. | 606/41 |
| 5,817,092 | 10/1998 | Behl | 606/41 |
| 5,827,268 | 10/1998 | Laufer | 606/28 |
| 5,863,290 | 1/1999 | Gough et al. | 606/41 |
| 5,868,740 | 2/1999 | LeVeen et al. | 606/41 |

OTHER PUBLICATIONS

O'Reilly, Kevin, Endovenous Diathermy Sclerosis as a Unit of The Armamentarium for the Attack on Varicose Veins; The Medical Journal of Australia, Jun. 1, 1974, p. 900.

Watts, G.T., Endovenous Diathermy Destruction of Internal Saphenous, British Medical Journal, Oct. 7, 1972, p. 53.

O'Reilly, Kevin, Endovenous Diathermy Sclerosis of Varicose Veins, The Australian, New Zealand Journal of Surgery, vol. 47, No. 3, Jun. 1977, pp. 393–395.

O'Reilly, Kevin, , A Technique of Diathermy Sclerosis of Varicose Veins, The Australian, New Zealand Journal of Surgery, vol. 51, No. 4, Aug. 1981, pp. 379–382.

Cragg et al., Endovascular Diathermic Vessel Occlusion, Diagnostic Radiology, 144: 303–308, Jul. 1982.

Ogawa et al., Electrothrombosis as a Treatment of Cirsoid Angioma in the Face and Scalp and Varicosis of the Leg, Technical Notes, No. 3, Oct., pp. 310–311.

Brunelle, et al., A Bipolar Electrode Vascular Electrocoagulation with Alternating Current, Radiology, Oct. 1980, vol. 137, pp. 239–240.

Aaron, Electrofulguration for Varicose Veins, the Medical Letter on Drugs and Therapeutics, Jul. 12, 1968, vol. 10, No. 14, Issue 248, p. 54.

Gradman, Venoscopic Obliteration of Variceal Using Tributaries Monopolar Electrocautery, Journal of Dermatology Surgery Oncology, 1994, 20, pp. 482–485.

Inturri, Pathophysiology of Portal Hypertension, Journal of Vascular Technology 19(5–6):271–276, Sep.–Dec. 1995.

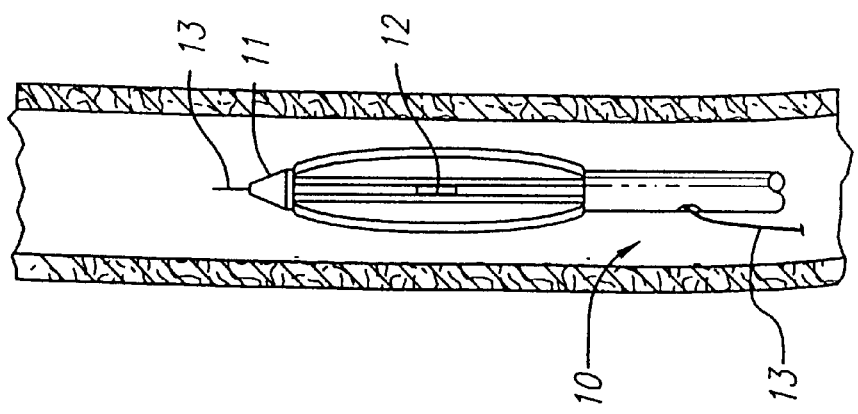
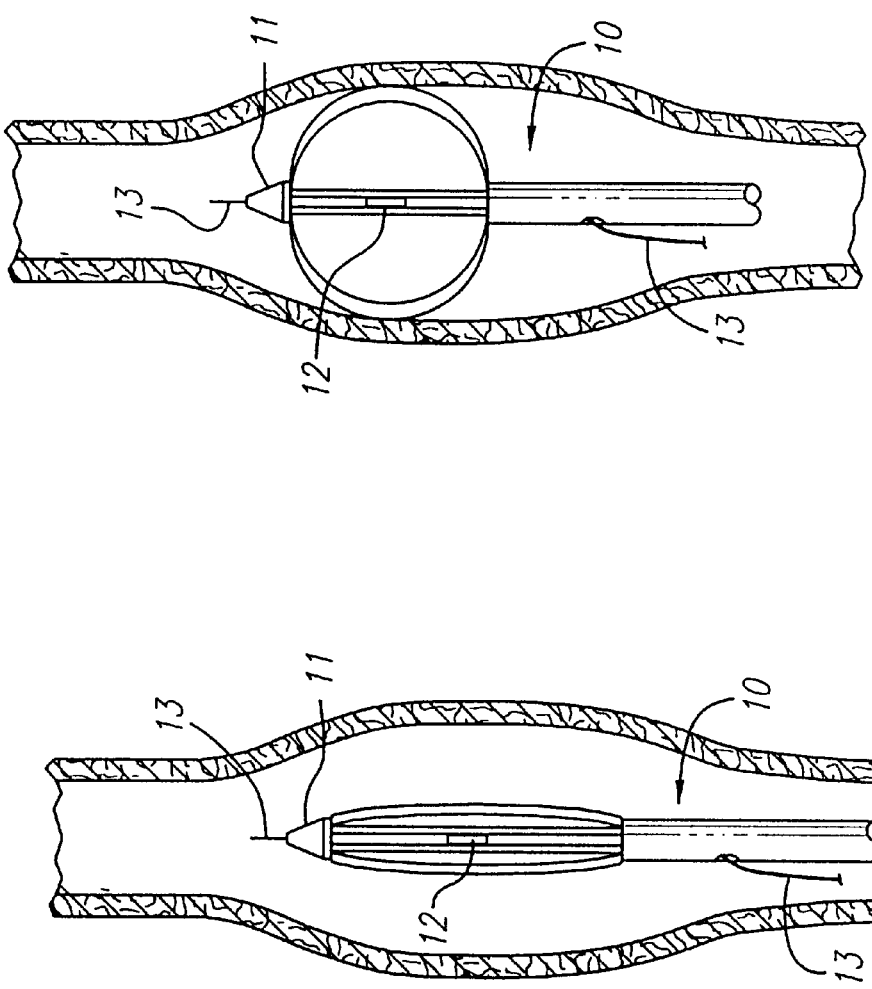

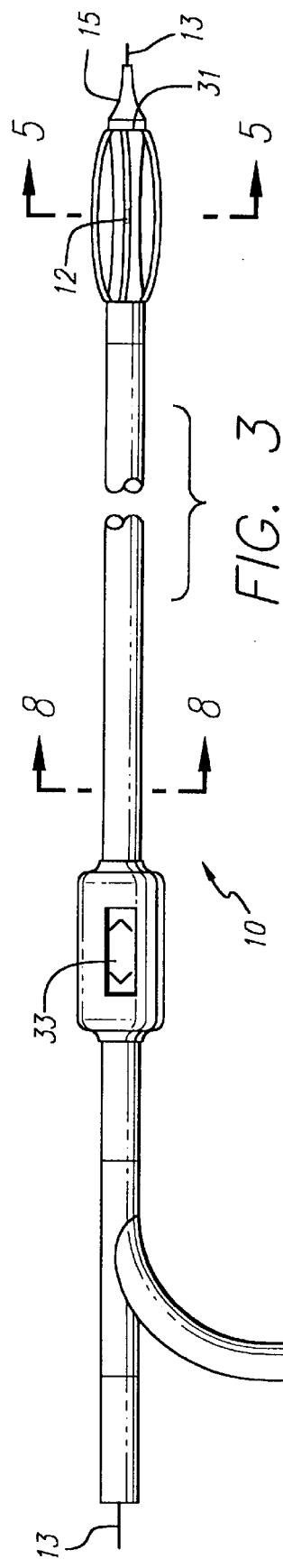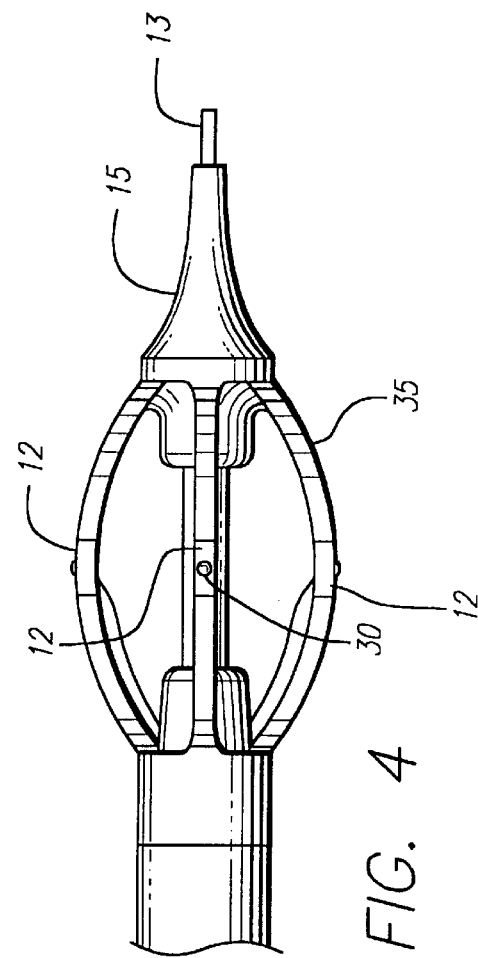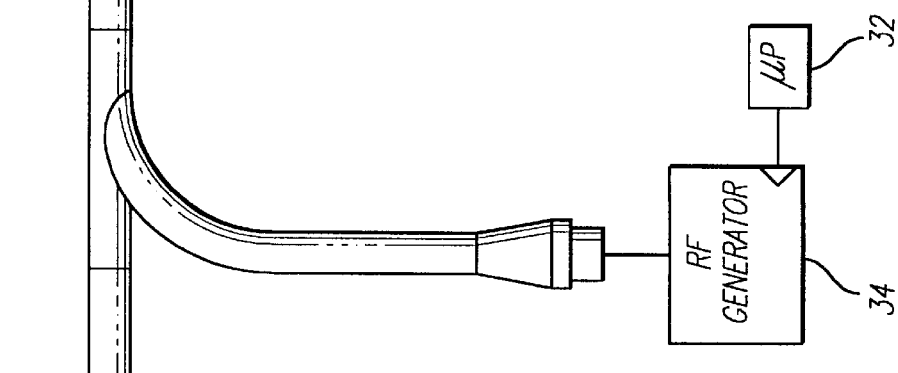

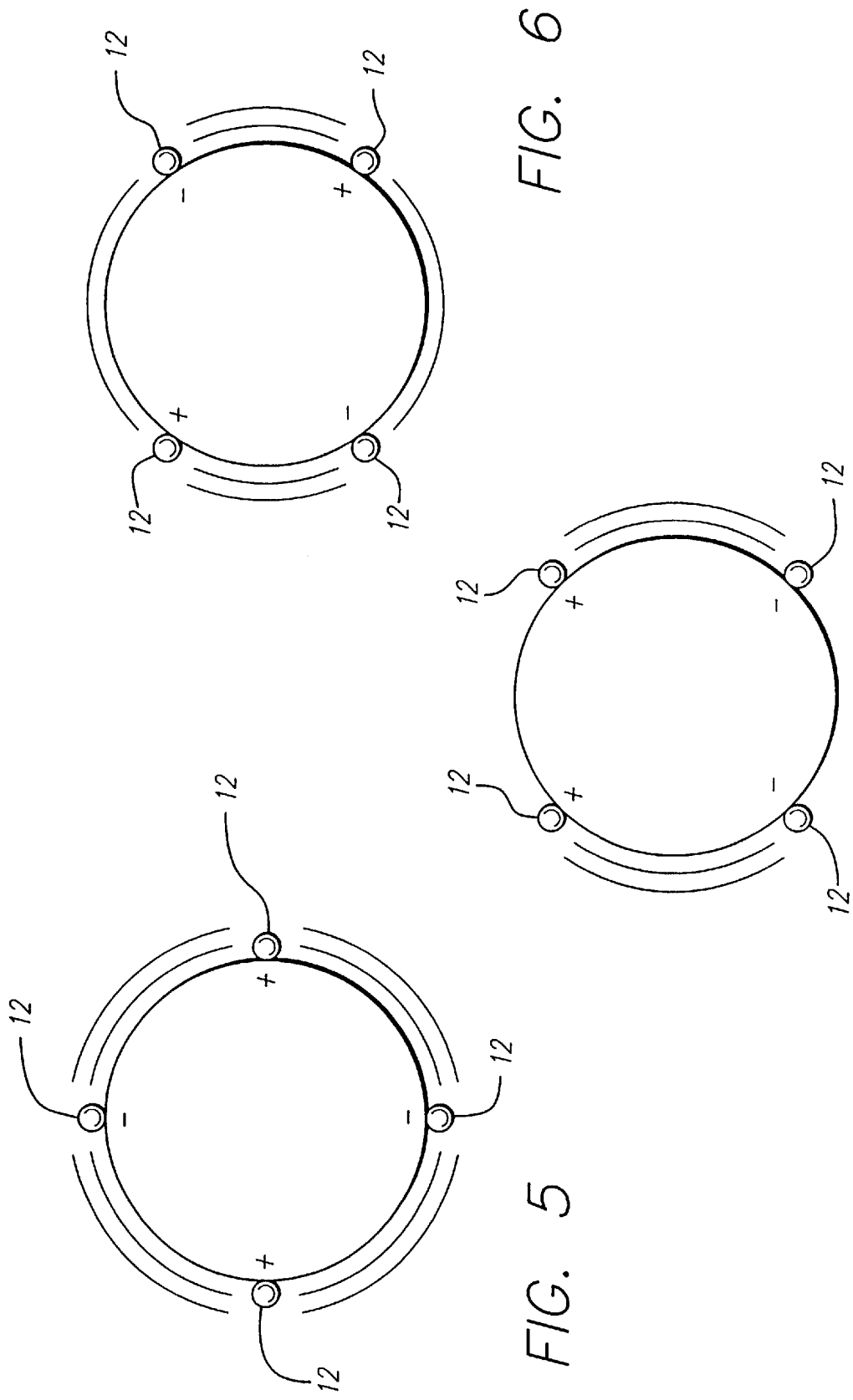

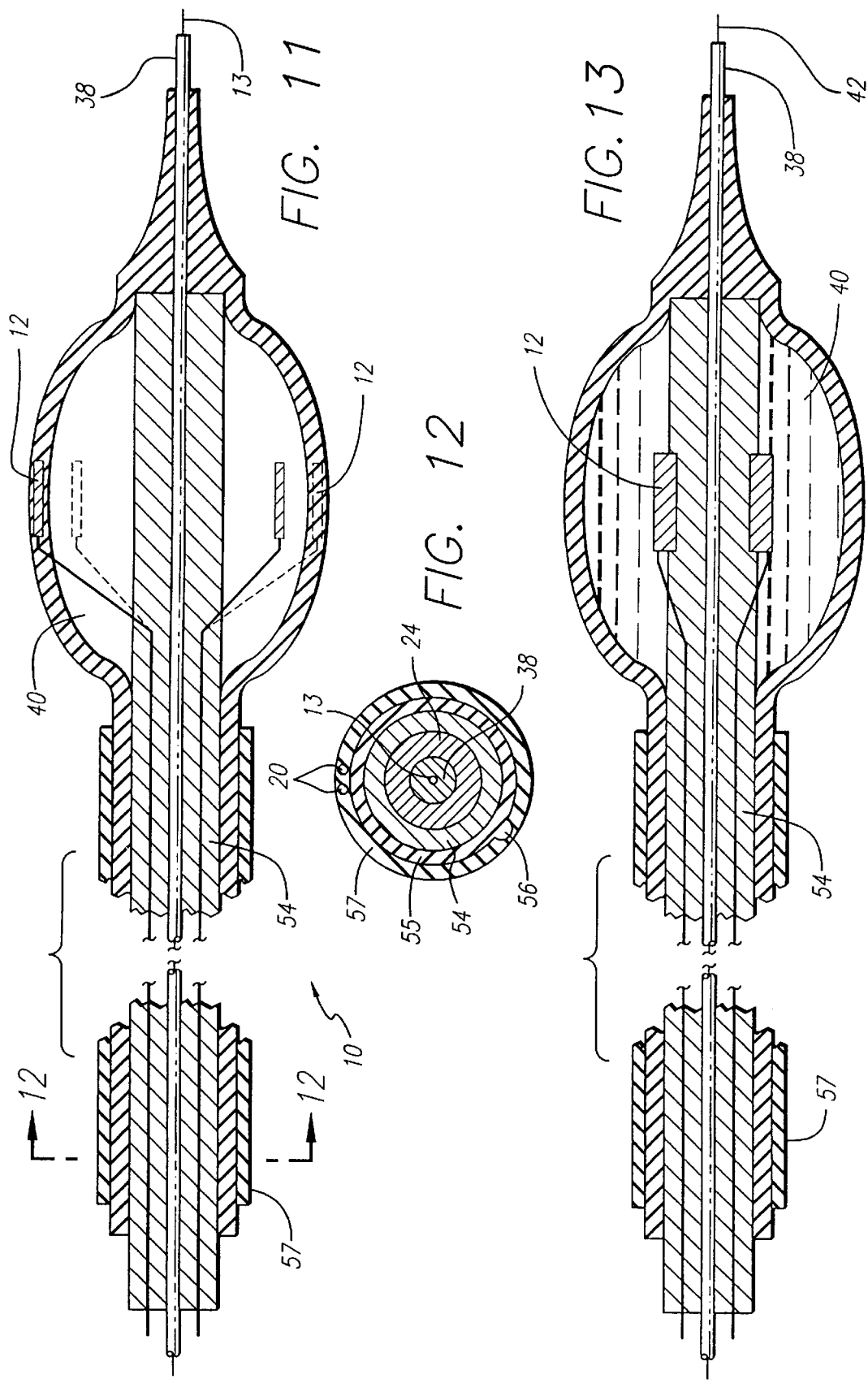

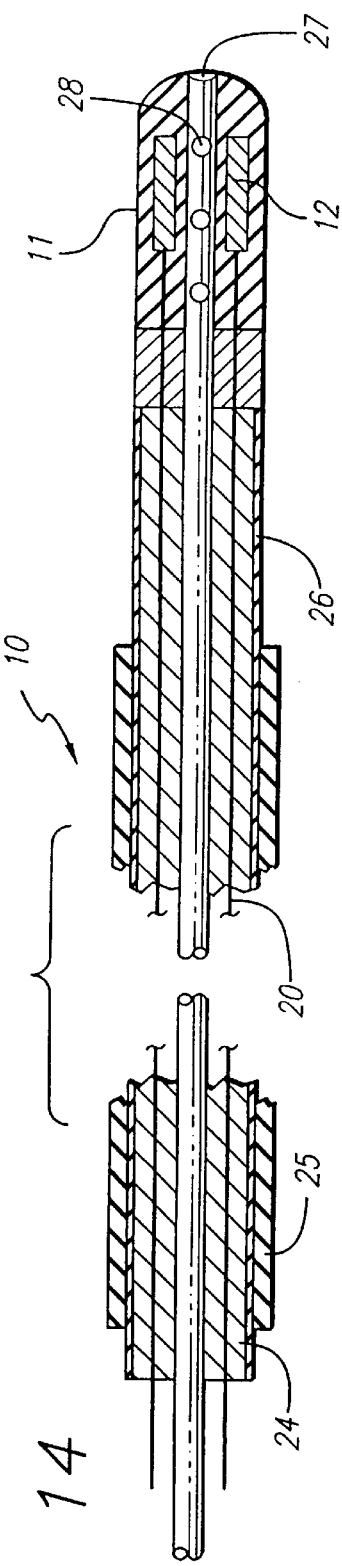
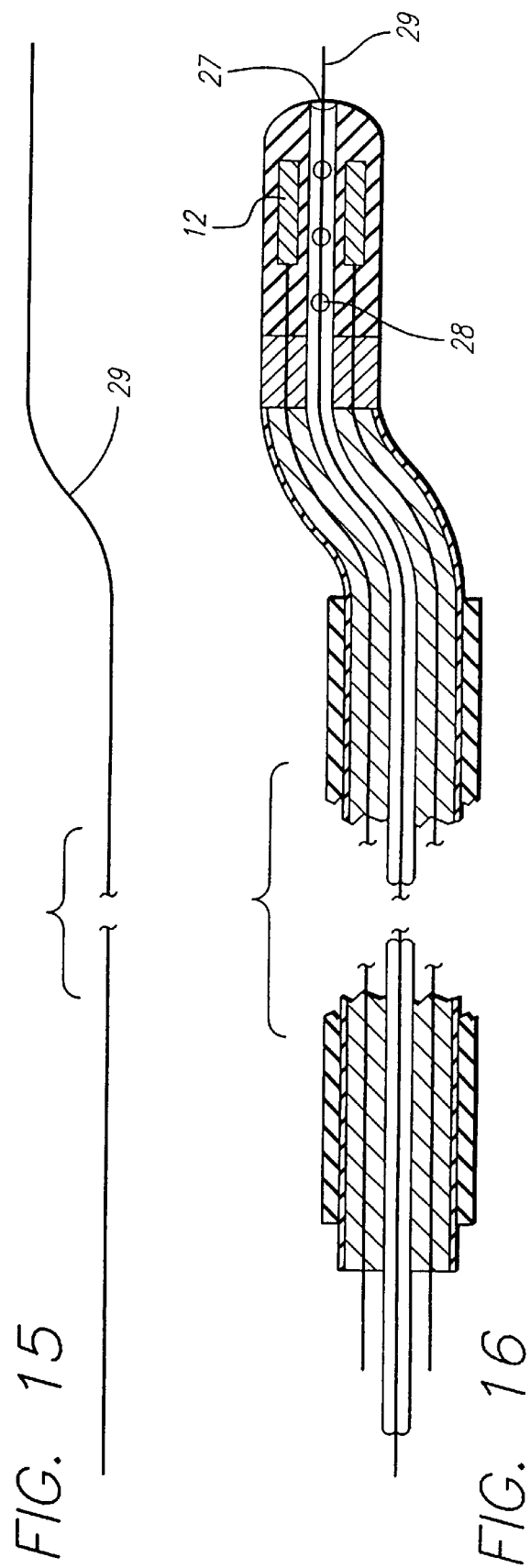
FIG. 14
FIG. 15
FIG. 16

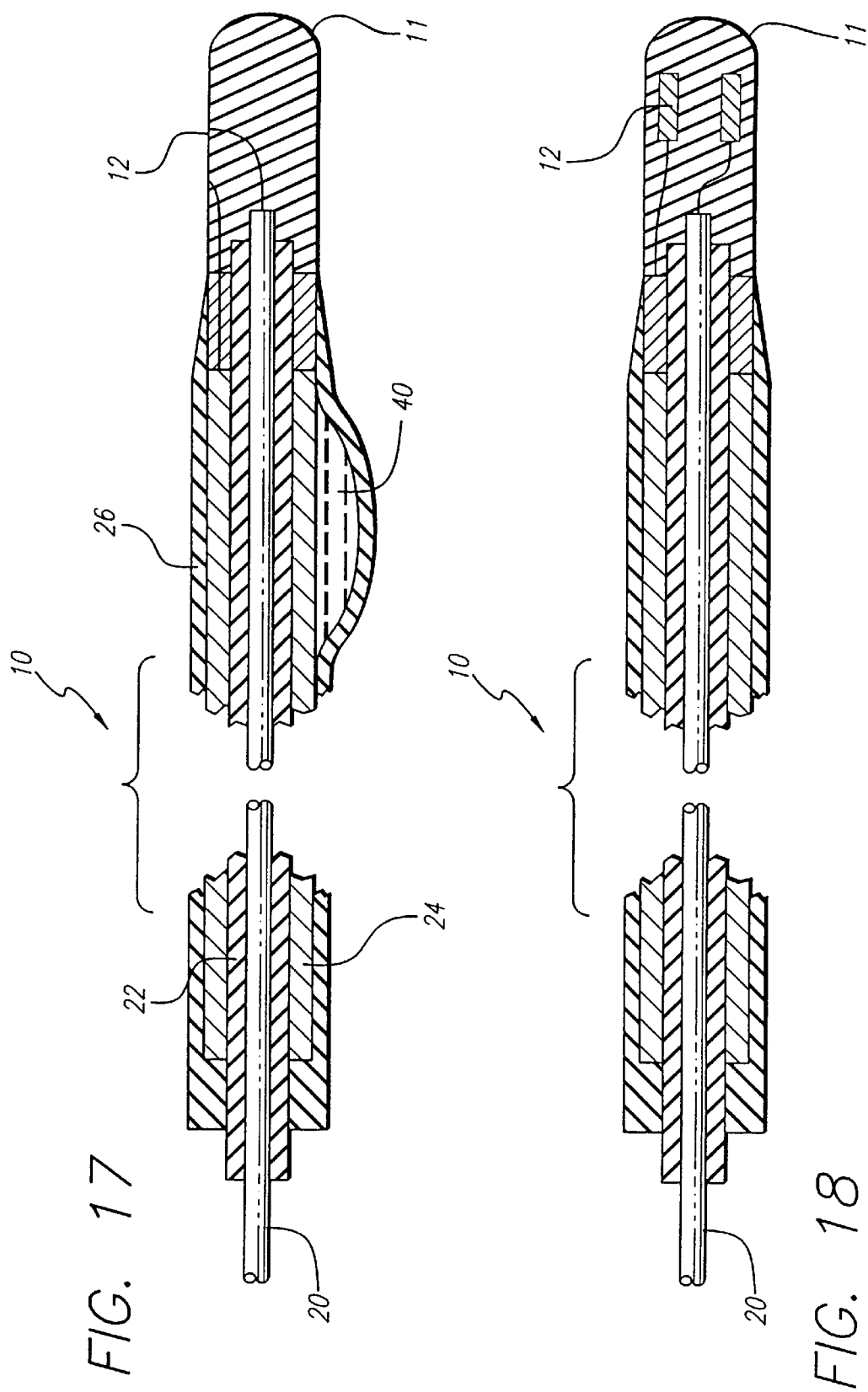

METHOD AND APPARATUS FOR TREATING ESOPHAGEAL VARICES

This application is a continuation-in-part of application Ser. No. 08/610,911, filed on Mar. 5, 1996.

BACKGROUND OF THE INVENTION

This invention relates to the treatment of esophageal varices, and more particularly to a minimally invasive procedure using a catheter-based system to intravenously deploy an electrode for providing radio frequency (RF) energy, microwave energy, or thermal energy to shrink a dilated vein to change the fluid flow dynamics and to restore the proper function of the vein.

Blood returns to the heart from the portal venous system through the veins surrounding the esophagus. Unlike other veins, such as the saphenous vein in the lower leg, the veins surrounding the esophagus typically do not have valves for bringing blood back to the heart. The venous pressure in these esophageal veins is relatively high, and blood can flow back to the heart without aid of venous valves.

Varicose veins may result from vein dilation, in which the vein walls weaken, stretch, and swell with additional blood. Varicose veins called esophageal varices can form in the venous system along the submucosa of the lower esophagus, and bleeding can occur from the dilated veins. Esophageal varices may result from portal hypertension and other abnormalities in the portal venous system, such as cirrhosis of the liver. Bleeding or hemorrhaging may result from esophageal varices, which can be difficult to stop and, if untreated could develop into a life threatening condition. Such varices can erode easily, and lead to a massive gastrointestinal hemorrhage.

Treatments for esophageal varices include portal-caval shunts, endoscope variceal ligation, sclerotherapy, and electrocoagulation from an electrode within the esophagus, such as from a tamponade device. The portal shunt involves the surgical joining of two veins, the portal vein and the inferior vena cava, to relieve pressure in the vein carrying blood into the liver. Although effective in eliminating recurrent hemorrhaging from varices, the attendant risks and complications of such invasive surgery, including encephalopathy and post-shunt hepatic failure, still exist for the portal shunt operation.

Endoscopic variceal ligation is analogous to rubber band ligation for treating hemorrhoids. The esophageal varices are ensnared with elastic bands to eradicate the varices. An endoscope is introduced into the patient and is placed adjacent to the esophageal varices to be treated. The varix is drawn into a drum attached to the tip of the endoscope. An elastic band mounted on the drum is then released over the varix. Endoscope variceal ligation may not achieve complete fibrosis of the inner wall of the esophagus, and recurrence of the varices may result. Other complications include bleeding from ulcers induced by the elastic bands, and esophageal obstruction due to occlusion of the lumen by banded esophageal varices.

In sclerotherapy, a solution, such as sodium morrhuate or ethanolamine, is injected submucosally into the tissue around the varicose vein in the esophagus to cause inflammation and scarring to close off the vein and reduce the likelihood of bleeding. Sclerotherapy, however, may create ulcerations which can lead to esophageal strictures.

Electrocoagulation has also been used to treat esophageal varices. A tamponade device having a metalized surface is introduced into the esophagus. The metalized surface is brought into contact with the mucous membrane of the esophagus. An electric current is then applied to the metalized surface to cause a thrombosing of the esophageal varices. This procedure may be employed to stop immediate hemorrhaging of the esophageal varices.

The prior treatments for esophageal varices typically involve external coagulation or obliteration of the veins, and often require multiple treatment sessions. Such treatments do not treat the varicosity directly, and may not affect the underlying causes which gave rise to the esophageal varices initially.

A need exists in the art to treat the dilated veins which give rise to esophageal varices and reduce venous pressure on the esophageal region from the portal vein system without the attendant risks of invasive surgery. Further need exists to provide a less invasive procedure which can treat multiple venous sites quickly and easily. The need exists to restore and normalize flow patterns, dynamics, and pressure, and shrink sections of dilated veins to a normal or reduced diameter. Where bleeding occurs, there is a need to achieve hemostasis in bleeding varices and minimize recurrence of bleeding.

SUMMARY OF THE INVENTION

Briefly, and in general terms, the present invention provides a minimally invasive method for solving the underlying problems of esophageal varices, and uses a system including a catheter for placing means for heating within a vein. The present invention involves a method of applying energy to cause shrinkage of a vein for treating esophageal varices, the method comprising the steps of introducing a catheter having a working end and means for heating located at the working end, to a treatment site in a vein; positioning the means for heating at the treatment site in the vein; applying energy from the means for heating to controllably heat the treatment site and cause shrinkage of the vein; and terminating the emission of energy from the means for heating after sufficient shrinkage of the vein has occurred so as to promote the proper function of the esophageal venous system.

An apparatus for performing the method of the invention comprises a catheter having a working end, means for heating a venous treatment area to cause shrinkage of the vein, wherein the means for heating is located at the working end of the catheter, and means for preventing further shrinkage after sufficient shrinkage of the vein, so that the vein continues to function.

In a more detailed aspect of an embodiment of the invention, electrodes are employed for heating and shrinking the vein. The electrodes generate a radio frequency field around the circumference of the catheter in order to shrink the vein wall circumferentially and omnidirectionally when the catheter electrode is positioned intraluminally within the vein. The field is controlled to maintain a specific temperature around the catheter in order to minimize coagulation within the vein, and to control the spread of heating within the venous tissue. The application and direction of RF energy to the venous tissue is capable of being controlled in order to achieve hemostasis in bleeding varices and minimize recurrence of bleeding.

A further aspect of a preferred embodiment is that the means for preventing further shrinkage include bowable members for controlling the outer diameter of the heating means to limit the amount of shrinkage. The bowable members that can be deflected radially outward for maintaining contact with the venous tissue.

An additional aspect of the preferred embodiment is that the bowable members are conductive so as to act as electrodes, and are substantially covered by an insulating material, except for the portion which is to come into apposition with the venous tissue. The bowable members maintain the electrodes in apposition to the venous tissue to ensure that the heating effect is delivered towards the venous tissue, and not the blood moving through the vein.

These and other aspects and advantages of the present invention will become apparent from the following more detailed description, when taken in conjunction with the accompanying drawings which illustrate, by way of example, the preferred embodiments of the invention.

BRIEF DESCRIPTION OF THE DRAWINGS

FIGS. 2a, 2b and 2c are side views of an embodiment of the catheter constructed and delivered to a venous treatment site within a dilated vein for treatment in accordance with the present invention;

FIG. 3 is a side view of an embodiment of the catheter having bowable electrodes in accordance with the invention;

FIG. 4 is a side view of the working end of the catheter illustrated in FIG. 3, and having bowable electrodes which deflect outwardly for increasing the effective diameter at the working end of the catheter in accordance with the present invention;

FIG. 5 is a cross-sectional view along lines 5—5 of FIG. 3, and depicts a catheter having four equidistantly spaced electrodes in accordance with the present invention;

FIG. 6 is a cross-sectional view of another embodiment of the catheter depicted in FIG. 5, this embodiment having four electrodes preferentially spaced to form two pairs of electrodes in accordance with the present invention;

FIG. 7 is a cross-sectional view of another embodiment of the catheter shown in FIG. 5 having two pairs of opposing electrodes in accordance with the present invention;

FIG. 11 is a partial cross-sectional side view of an embodiment of an over-the-wire balloon catheter having four equidistantly spaced apart electrodes on the surface of the balloon in accordance with the present invention;

FIG. 12 is a cross-sectional view taken along the lines 12—12 of the over-the-wire balloon catheter in FIG. 11;

FIG. 13 is a partial cross-sectional side view of another embodiment of the catheter having electrodes located within the balloon portion in accordance with the present invention;

FIG. 14 is a cross-sectional side view of another embodiment of the catheter having a bendable tip;

FIG. 15 is a side view of a deflection wire which can be used in conjunction with the catheter shown in FIG. 14.

FIG. 16 is a cross-sectional side view of the catheter of FIG. 14 and the deflection wire of FIG. 15, having a bendable tip which deflects laterally for causing apposition between the electrodes of the catheter and the vein wall in accordance with the present invention;

FIG. 17 is a cross-sectional side view of another embodiment of the catheter having a balloon on one side of the catheter and longitudinal electrodes on the other side at the working end of the catheter for moving the electrodes into appositional contact with the vein wall in accordance with the invention;

FIG. 18 is cross-sectional top view of the embodiment of the catheter in FIG. 17 in accordance with the present invention;

DETAILED DESCRIPTION OF PREFERRED EMBODIMENTS

Figure 1:
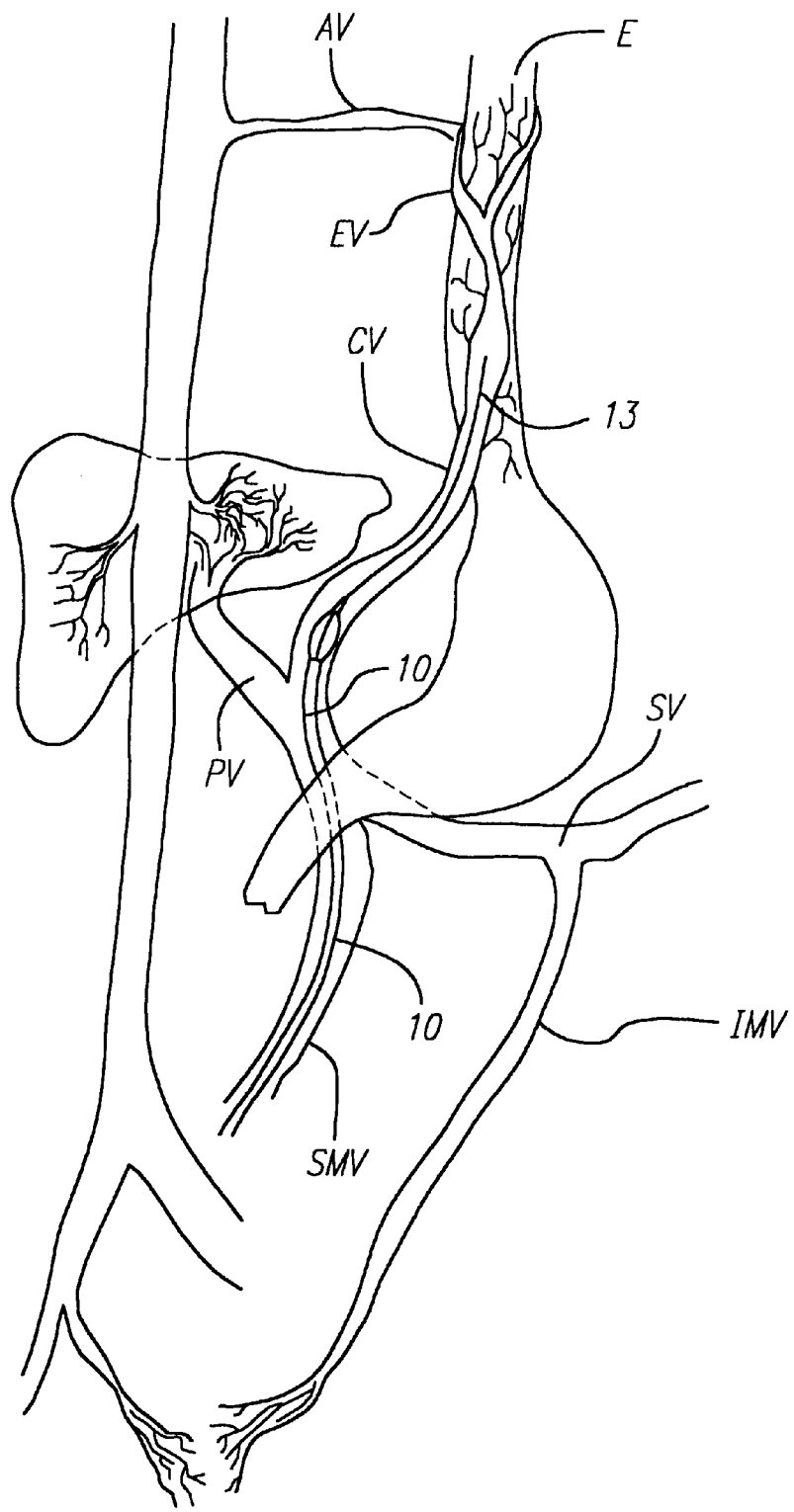
FIG. 1 is a partial profile view of the anatomical region of the esophageal region, including a vein to be treated in accordance with the present invention.

As shown in the exemplary drawings, the invention is embodied in a system for the intravenous treatment of veins using a catheter to deliver at least one electrode to a venous treatment site. Although described as applying RF energy from the electrode, it is to be understood that other forms of energy such as microwaves, ultrasound, direct current, circulating heated fluid, radiant light, and lasers may be used, and that the thermal energy generated from a resistive coil or curie point element may be used as well. As used herein, like reference numerals will designate similar elements in the various embodiments of the present invention to be discussed. In addition, unless otherwise noted, the term "working end" will refer to the direction toward the treatment site in the patient, and the term connecting end will refer to the direction away from the treatment site in the patient.

The catheter 10 delivers at least one electrode 12 at the working end 11 of the catheter to a venous treatment site in order to restore the proper function of a vein leading to the esophageal region. An over-the-wire or rail wire guided catheter is used to deliver the one or more electrodes through the venous system to the esophageal treatment site. The catheter may include a single RF electrode for monopolar heating where an external electrode having a large surface area is placed on the skin. In a bipolar arrangement, two or more RF electrodes are be situated at the working end 11 of the catheter 10. The catheter 10 and the electrodes 12 may be configured for either arrangement. Further, the catheter 10 and the electrodes 12 should be constructed from materials which are opaque to fluoroscopy, x-ray, ultrasound, or other imaging systems. This and other embodiments of the catheter 10 will be described in greater detail later. Particular discussion will be directed to the treatment of dilated veins in the esophageal region using RF energy, although the method of the present invention is well suited to treating veins in other areas of the body.

Varicose veins called esophageal varices can form in the venous system along the submucosa of the lower esophagus, and bleeding can occur from the swollen veins. A properly sized catheter 10 is used to deliver the electrodes 12 to the site of venous dysfunction along the esophageal varices. Endovascular access for the catheter is preferably provided through the superior mesenteric vein or portal vein to shrink the portal vein branches leading to the lower esophagus. Proper positioning of the electrode within the vein may be confirmed using fluoroscopic or ultrasound techniques. The electrodes apply RF energy or other forms of energy at a suitable power or frequency to shrink the vein and reduce the swelling and transmission of high portal venous pressure to the veins surrounding the esophagus while maintaining the function of the vein. The amount of shrinkage of the vein is limited by the diameter of the catheter itself, and the catheter or electrodes themselves may be expanded to a predetermined diameter which limits shrinkage of the vein to that diameter.

When treating the veins of the lower esophageal region, the access site is prepped and a percutaneous introducer is inserted into the vein. The procedure for the repair of incompetent veins may be accomplished by a qualified physician with fluoroscopic guidance or ultrasonic observation, or direct visualization. A guide wire 13 is passed into the vein through the introducer, and advanced through to the venous treatment site. The wire is advanced to the venous treatment site, such as the level of the most proximal incompetent vein site which is to be repaired. Preferably, the guide wire and catheter are advanced antegrade to the esophageal treatment site. Alternatively, the catheter may be inserted into the vein directly and manipulated without a guide wire.

As shown in FIG. 1, in a partial view of the venous system leading to the esophageal region, the catheter 10 is advanced over the guide wire 13 to a dilated section of the vein. One method of delivering the catheter and guide wire is to introduce the guide wire through the superior mesenteric vein SMV to the portal vein PV and coronary vein CV which branches and leads to the lower esophagus E to form the esophageal veins EV. As an alternate route, the guide wire could be introduced into the inferior mesenteric vein, and routed through the splenic vein SV, the portal vein PV, and the coronary vein CV to arrive at the esophageal varix to be treated.

The guide wire is deployed and manipulated so as to reach the treatment site for treating the esophageal varices. The venous treatment site is preferably within the lumen of a dilated vein. The catheter 10 is then delivered to the venous treatment site over the guide wire 13 as shown in FIG. 2. Fluoroscopy, x-ray, ultrasound, or a similar imaging technique could be used to direct the specific placement of the catheter and to confirm position within the vein. X-ray contrast material may be injected through or around the catheter to identify the dilated venous sections to be treated. Hemorrhaging or bleeding of the esophageal varices may also be identified in this manner.

Once the dilated venous section is reached, the one or more electrodes 12 are activated to apply RF energy to the dilated venous section. While the electrodes may be maintained in the center of the vein, the electrodes are preferably placed in apposition with the vein wall. The electrodes in apposition with the venous tissue ensures that the heating effect is delivered towards the venous tissue, and not the blood moving through the vein, and allow control over the shrinkage of the vein. One method of achieving apposition is by bowing the electrodes out away from the body of the catheter, as shown in FIG. 3. The electrodes have an elongate longitudinal structure having opposite ends attached to a stationary and a moveable portion, respectively, at the working end of the catheter. The bowable electrodes are actuated by moving the outer sleeve of the catheter while maintaining the tip of the catheter stationary. Alternately a central wire could be used to move the tip while keeping the opposite end of the bowable electrode in place.

The one or more electrodes 12 at the working end 11 of the catheter 10 apply RF energy once properly positioned and apposed at the venous treatment site to cause shrinkage of the vein. An RF generator is activated to provide suitable RF energy to the electrodes, preferably at a low power level, and preferably at a selected frequency from a range of 250 kHz to 350 MHZ. For example, one suitable frequency is 510 kHz. One criteria for the selection of the applied frequency is to control the spread, including the depth, of the thermal effect in the tissue. Another criteria is compatibility with filter circuits which can be used to eliminate RF noise from thermocouple signals.

The energy emitted from the electrodes is converted within the venous tissue into heat. As the temperature of the venous tissue increases, the venous tissue begins to shrink. The shrinkage is due in part to dehydration and the structural transfiguration of the collagen fibers in the vein. Although the collagen becomes compacted during this process, the vessel with collagen still retains elasticity.

Substantial shrinkage may be achieved very rapidly, depending upon the specific treatment conditions, including the diameter of the vein being treated and power level of the applied RF energy. The properties of the treatment site, such as temperature, may be monitored to provide feedback control for the RF energy. Other techniques, such as impedance monitoring and ultrasonic pulse echoing, may also be utilized in an automated system which shuts down the application of RF energy from the electrodes to the venous section when sufficient shrinkage of the vein is detected and to avoid overheating or cauterization of the vein. Monitoring these values in an automatic feedback control system for the RF energy may also be used to control the heating effect.

Sufficient shrinkage of the vein may be detected by fluoroscopy, external ultrasound scanning, intravascular ultrasound scanning, impedance monitoring, temperature monitoring, direct visualization using an angioscope, or any other suitable method. For example, the catheter 10 may be configured to deliver x-ray contrast medium to allow visualization by fluoroscopy for assessing the condition of the vein and the relationship of the catheter to the treatment area of the vein during the shrinkage process. As an alternative to fluoroscopy, external ultrasound techniques such as B-scanning using distinct ultrasound signals from different angles, or intravascular ultrasound may be used to acquire a more multidimensional view of the vein shrinkage at the treatment site, which improves the detection of uneven shrinkage in the vein. An angioscope may also be used to directly visualize and determine the extent and degree of vein shrinkage.

The working end 11 of the catheter 10 near the electrodes 12 physically limits the amount of shrinkage. The electrodes 12 at the working end 11 are bowed outwards into apposition with the vein wall, and then gradually reduced inwardly towards the catheter during the application of RF energy. The final effective diameter of the electrodes 12 at the working end 11 is preferably sufficient to prevent the complete occlusion of the vein. Other schemes, such as an inflatable balloon, may be used to mechanically limit or control the amount of shrinkage in the vein to a desired diameter. RF energy is no longer applied from the electrodes after there has been sufficient shrinkage of the vein to alleviate the dilation of the vein. Methods other than the aforementioned mechanical methods may also be used to control the magnitude of vein shrinkage. Such non-mechanical methods include controlling the time and temperature of the venous RF treatment.

The dilated venous section is heated and shrunk to a normal or reduced diameter under the controlled application of RF energy in accordance with the present invention. A contiguous axial section of dilated vein may be treated by applying RF energy along the dilated venous section, even if the section is extensive. To treat an extensive venous section, the catheter is moved in intervals to progressively shrink the venous section, or moved back and forth along the extensive section during the application of RF energy. Further, thickening of the vein may occur during treatment, and reduce the likelihood of the recurrence of vein dilation and bleeding.

Applying RF energy shrinks the dilation of esophageal varices, and extending the shrinkage to include other sections in the portal venous system can be advantageous in further lessening the effect of increased venous pressure on the esophageal varices. Esophageal veins can be sensitive to pressures from the portal system. Treatment of the branches of the portal vein before the esophagus by general shrinkage along an extensive section of the vein before the esophagus can reduce the dilating effect on the esophageal veins caused by increased pressures from the portal venous system.

It is to be understood that other mechanisms may be employed to position or appose the electrodes with the venous section to be repaired without bowing or expanding the electrodes away from the catheter itself. The catheter may be made capable of being deflected, torqued, or otherwise moved to allow for the proper placement of the electrode. The catheter may be manufactured to provide a controllable bend near the working end. For example, the bend may be formed from a shape-memory metal, manipulatable by a system of wires, a torquable braid, or a permanent bend in the catheter. Manipulating the working end of the catheter enables preferential heating along the vein wall being treated, if desired, where the electrodes are placed closer to one side of the vein wall. Preferential heating of the vein can also be used to effect hemostasis.

Where the catheter is provided with a fluid delivery lumen, a cooling fluid is delivered through the delivery lumen to the bloodstream during RF heating of the vein being treated. The fluid may include contrast material for assessing the condition of the vein. The delivered cooling fluid minimizes any heating effect on the blood, and reduces the risk of heating the blood to the point of coagulation. The fluid may be delivered through ports formed along the side of the catheter near the working end and the electrodes.

After treating one dilated venous section, the catheter 10 is repositioned within the vein so as to treat as many venous sections as necessary. RF energy is applied to each venous section to be repaired, until all of the desired venous sections are treated. Multiple dilated venous sections may be treated and repaired in a single minimally invasive procedure. If desired, a second introducer is inserted into the patient in order to treat incompetent venous sections in the other vein systems.

One embodiment of the catheter 10 having electrodes 12 on the working end 11 which causes localized heating of the surrounding venous tissue and shrinkage of the vein is shown in FIG. 3. The catheter 10 includes electrodes 12 in the form of four conductive elongate members which can be bowed outward. The bowable electrodes are formed along the circumference of the catheter, but are not fixed to the catheter. The catheter itself is fit through a suitably sized sheath for the procedure. For example, a 7 French sheath, which has about a 2.3 millimeter (mm) diameter, may be used. The sheath is composed of a biocompatible material with a low coefficient of friction. The working end 11 of the catheter includes a tip 15 which is attached to one end of each electrode, and the other end of each electrode is connected to a sliding sleeve 36 formed along the exterior of the catheter shaft. The outer sleeve extends down the length of the catheter to allow the physician to directly and mechanically control the effective electrode diameter during the application of RF energy. As the the slidable sleeve 36 is moved towards and away from the working end in response to a control actuator 33, the electrodes 12 are urged radially outwards and inwards, respectively. The tip 15 essentially remains stationary while the slidable sleeve is moved. Moving the sleeve 36 back toward the connecting end of the catheter pulls back and flattens the electrodes against the catheter before insertion or withdrawal from the vein. Moving the sleeve 36 forward toward the working end of the catheter causes the electrodes to deflect and radially bow outward to an increased diameter. The contact area of the electrodes is bowed outwardly as the opposite ends of the longitudinal electrode are moved closer together. The outer sleeve may be moved a preset distance to cause the electrodes to bow outwardly to a known diameter. Bowing the electrodes outwardly also places the electrodes in apposition with the venous tissue to be treated. By manipulating the slidable sleeve to adjust the effective diameter of the catheter defined by the radial bowing of the electrodes, contact between the electrodes and the vein wall can be maintained as the vein shrinks. The control actuator 33 is a switch, lever, threaded control knob, or any other suitable mechanism, preferably one which can provide fine control over the movement of the slidable sleeve. By using the control actuator to move the slidable sleeve, the effective diameter of the electrode can be controlled for treating vein lumen having different diameters, and for providing varying degrees of vein shrinkage.

The tip 15 has a nosecone shape, or can have any shape which allows tracking of the catheter over the guide wire and through bends in the venous vascular system. The nosecone tip can be fabricated from a polymer having a soft durometer, such as 70 Shore A. Alternatively, the nosecone can be constructed from a spring covered with a thin layer of polyethylene shrink tubing.

The extent of shrinkage is controlled by the effective diameter of the catheter and the electrode combination. The electrodes 12 are bowed radially outward as part of the effective diameter of the catheter so as to come into apposition with the vein wall. After being placed in contact with the venous tissue, and the effective diameter could be mechanically reduced to control shrinkage while RF energy was being applied. The electrodes 12 are preferably operated as bipolar electrodes. As RF energy is applied to the electrodes, an RF field is created around the effective diameter of the catheter as defined by the bowed electrodes, and the vein becomes heated and begins to shrink. The effective diameter of the catheter is reduced under the control of the physician to control the amount of shrinkage. As the effective diameter is decreased, the electrodes continue to maintain apposition with the venous tissue. The extent of vein shrinkage is monitored by fluoroscopy, or any other suitable method. After shrinking the vein to the desired diameter, the application of RF energy from the electrodes 12 is ceased. The desired diameter of the vein is the final effective diameter of the catheter, as defined by the deflected electrodes 12.

The electrodes 12 have an elongated shape and may be fabricated from stainless steel, spring steel, or nitinol, so that the electrodes 12 would be biased to return to a reduced diameter profile. The electrodes are rounded wires to facilitate flexing of the catheter at the working end while being delivered through the bands of tenuous venous vasculature. The diameter of the electrodes are preferably between about 0.005 to 0.015 inches (about 0.12 to 0.35 mm), but can be up to about 0.03 inches (about 0.7 mm). Other shapes including rectangular wires having relatively large flat surfaces for contacting the vein wall can be used. Such rectangular wires can have widths ranging from 0.005 to 0.05 inches, and preferably between 0.015 and 0.030 inches, to allow four to eight electrodes around the catheter shaft.

The entire length of the bowable longitudinal electrode is conductive, and insulation 35 is provided over the majority of the electrode surface, as shown in FIG. 4, in order to prevent any unintended heating effects. Only a modest portion of the conductive surface is exposed to act as the electrode. The heating effect is greatest when the electrodes are close together since the electrical field density (power density) is greatest at this point. The ends of the electrodes are insulated from each other to prevent creating electrical field densities that are larger at the ends compared to that around the middle of the electrode. As the effective diameter increases, even greater field disparities between the ends and the outwardly bowed midsections could be created if no insulation were provided. The insulation 35 can be polyimide, paralyene, or another type of insulating material. The insulation 35 provided along the sides and the back of the electrodes opposite from the vein wall further prevents heating of the blood flowing in the vein, which should also reduce the likelihood of coagulation. Where the wire has a rectangular shape, then the exposed area which functionally acts as the electrode would then occupy only one face of that wire. The insulation 35 surrounding the electrode can further cover the peripheral edges of the exposed face of the electrode to further isolate the blood flow from unintended heating effects.

The exposed area of the electrode is preferably the area which directly contacts the vein wall during apposition. The heating effect is then focused into the vein wall. The exposed surface area of the electrode should be as great as allowable while maintaining a consistent distance between the exposed sections of the electrode along the circumference of the effective diameter. The larger the exposed surface of the electrodes apposed against the vein wall during shrinkage, the greater the surface area of the vein wall affected by the electric field generated by the electrodes. The exposed area for the electrode can be substantially flat to enhance uniform contact with the vein wall and for controlling the diameter of the vein.

A sensor 30 such as a small thermocouple for measuring temperature is attached to the electrode 12. The temperature sensor 30 is soldered in place through a hole in the electrode so that the sensor is nearly or substantially flush with the exposed surface of the electrode. The sensor can accurately sense the temperature of the vein wall in apposition with the exposed electrode surface. The leads to the sensor are situated on the opposite side of the electrode which is insulated.

A cross-sectional view of the electrodes 12 of FIG. 3 along lines 5—5 is shown in FIG. 5. In the four-electrode configuration, a preferred embodiment is to have the electrodes 12 spaced equidistantly apart along the circumference of the catheter. Although the catheter has been described as having a four electrode configuration, it is to be understood that the catheter may include a different number of electrodes, for example, six, eight, or more bowable electrodes, in order to lessen the inter-electrode gap and reduce the amount of power required to heat the venous tissue. The polarity of each electrode is preferably opposite to the polarity of the immediately adjacent electrodes to provide for omnidirectional and circumferential shrinkage of the vein. Thus, a relatively uniform RF field would be created along the circumference of the catheter by the alternating electrodes. In another embodiment, as shown in FIG. 6, if adjacent electrodes were to be moved closer together, two effective pairs of active electrodes of opposite polarity would be formed along the circumference of the catheter. While an RF field would still be formed along the entire circumference of the catheter, the RF field would be strongest between the closest adjacent electrodes of opposite polarity. Shrinkage of the vein would be concentrated where the RF field was strongest. In another embodiment, the RF field may be further focused directionally using two pairs of electrodes arranged so as to be isolated from one another. For example, as shown in FIG. 7, the positive electrodes of each electrode pair would be adjacent to one another, and no field is formed along the circumference of the effective diameter between the two pairs of electrodes. Opposing RF fields are established by the two pairs of electrodes to create two discrete heating zones along the circumference. These heating zones may be directed to cause heating at isolated areas within the vein (i.e., not circumferentially) so as to direct treatment to the specific area of variceal bleeding from the vein. Specific or isolated instances of variceal bleeding may be treated by such directional application of RF energy to the vein.

It is to be understood that although a bipolar arrangement is described, a monopolar arrangement may also be used. In a monopolar arrangement, an inside electrode, such as a mesh or wire electrode, is inserted into a patient's body. An outer electrode having a much larger surface area than the inside electrode is placed on the outer surface of the patient's body near the treatment site. For example, an external metal plate is placed on the skin over the region to be treated by the inside electrode. Alternatively, a metalized balloon is introduced into the esophagus and inflated to come into contact with the mucosal lining of the esophagus to act as the inactive return electrode. The electrodes are connected to a RF generator which produces an electric field within the patient's body. Because the surface area of the inner electrode is much smaller than that of the outer electrode, the density of the electric field is much higher around the inside electrodes. The electric field reaches its highest density between the two electrodes in the region near the inside electrode. The increased density of the field around the inside electrode allows localized heating of the tissues surrounding the inside electrode. The degree of heating may be dependent on such factors as the impedance and dielectric constant of the tissue being heated. It is to be understood that different numbers and configurations of electrodes can be used to produce the desired discretionary heating effect.

Figure 8:
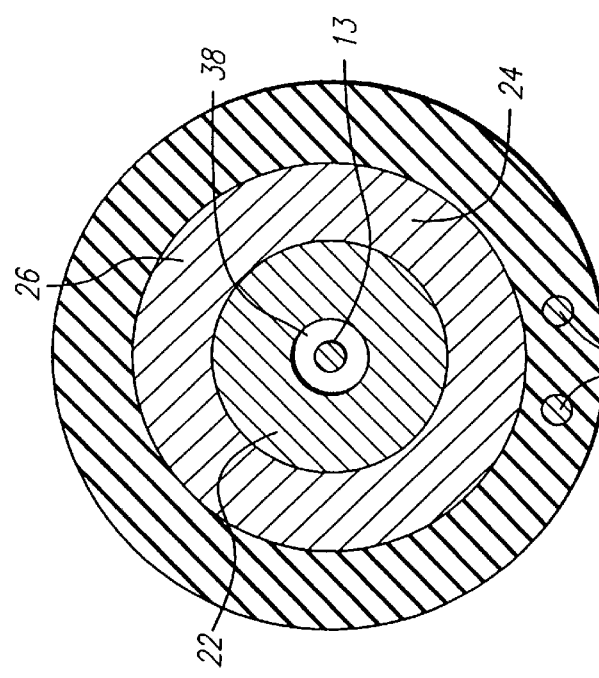
FIG. 8 is a cross-sectional view of an embodiment of the catheter along lines 8—8 of FIG. 3.

The working end of the catheter further includes a guide wire lumen for accepting the guide wire 13. The tip of the guide wire 13 is preferably rounded. The guide wire lumen 38 is preferably insulated so as to prevent or minimize any coupling effect the electrodes 12 may have on the guide wire 13. The guide wire can be removed before the application of RF energy to the electrodes. A cross-sectional view of the catheter 10 taken along lines 8—8 FIG. 3 is shown in FIG. 8. The guide wire 13 is shown centrally located within a guide wire lumen 38. The guide wire lumen 38 is surrounded by a layer of insulation material 22, which in turn is surrounded by a copper braid 24 for stability and stiffness, as well as for providing flexible torqueability to the catheter. An insulation sheath 26 covers the copper braid 24, and contains the conductive leads 20 to the electrodes as well. In a bipolar arrangement, the conductive leads 20 have opposing polarity. In an over-the-rail type catheter, the guide wire is outside the catheter until arriving at the working end of the catheter, upon which, the guide wire enters the guide wire lumen. The guide wire lumen 39 is preferably located within the insulation material 22 in order to electrically isolate the guide wire 13 from the electrodes 12. The guide wire lumen can also allow for the delivery or perfusion of medicant and cooling solution to the treatment area during application of the RF energy.

The sensors 30 are preferably located between the bowable electrodes 12 for measuring values such as impedance. In measuring impedance, as will be described in further detail later, the area between the electrodes often provides the most relevant data. It is to be understood that the sensors 30 may be used to measure other values including temperature and ultrasound signals. Further, the positioning of the sensors 30 on the catheter 10 may be varied depending on the value being measured. For example, when measuring temperature, it may be desirable to place the sensor on or immediately adjacent to the electrode. The temperature sensor senses the temperature of the tissue around the electrodes. When measuring echo signals of pulsed ultrasound, the sensors may be placed between the electrodes, or at the tip of the catheter. When measuring pulse echo ultrasound signals, the catheter is preferably rotated to resolve an image of the environment surrounding the catheter and the sensors.

Figure 19:
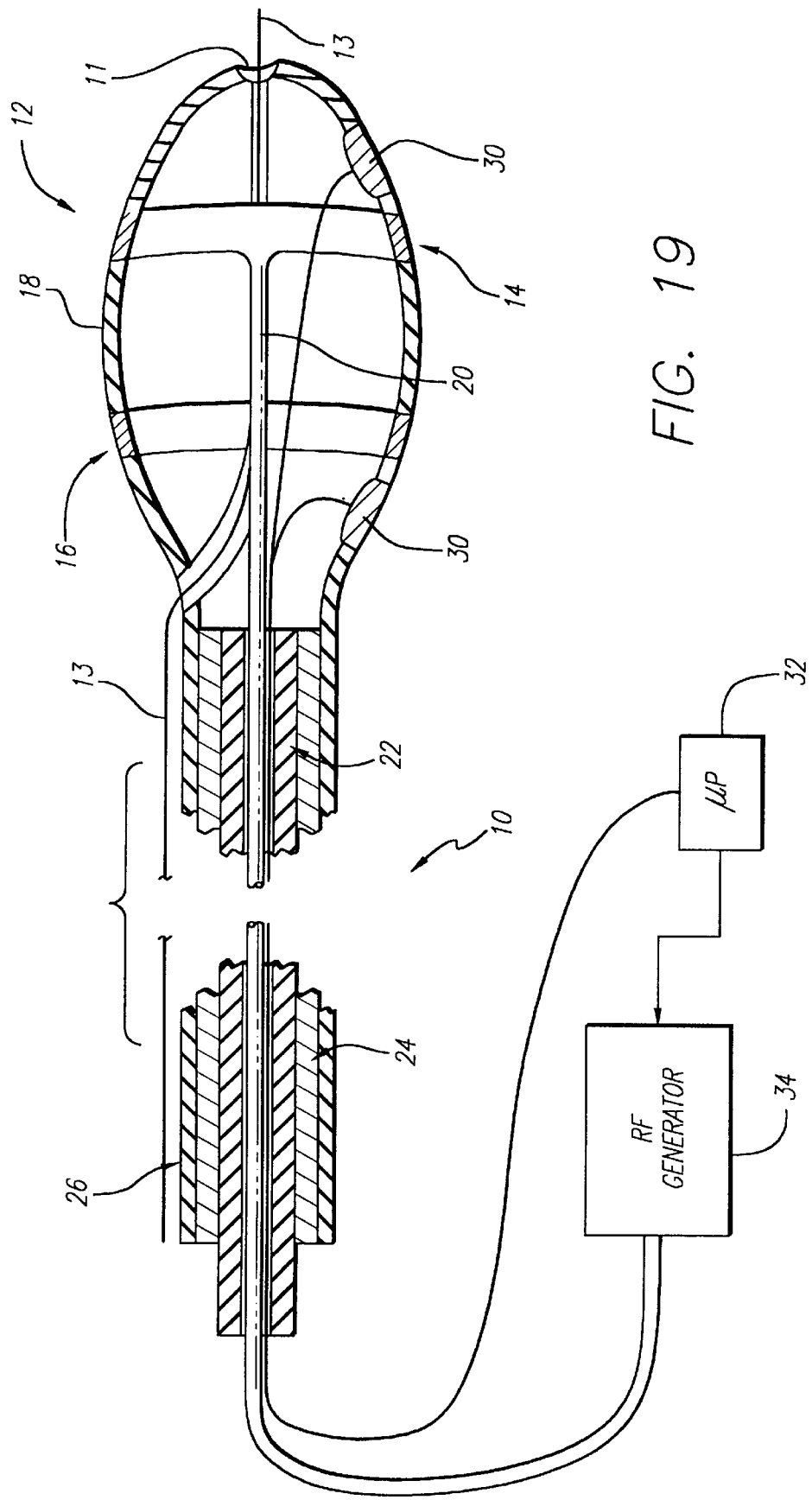
FIG. 19 is a partial cross-sectional side view of an embodiment of the catheter having a bulbous tip and ring electrodes for treating a dilated vein in accordance with the present invention.

The sensors 30 measure parameters used to determine the extent of vein shrinkage. For example, the sensors 30 may be sensing electrodes which measure the impedance of the venous tissue in contact between the end electrode 14 and the ring electrode 16 as illustrated in FIG. 19. A constant RF current is emitted from the active end electrode 14 to the return ring electrode 16. Also, the impedance may be measured between the electrodes 14 and 16 directly. The voltage across the electrodes is measured by the sensing electrodes to detect the impedance of the volume between the electrodes. The voltage measured is proportional to the impedance Z between the electrodes, where Z=V/I and the current, I, is constant. The impedance changes as a function of the diameter of the vein because there is less blood and less conductance as the venous diameter decreases. As the volume decreases due to shrinkage, the amount of conductive volume between the electrodes decreases, and the increased impedance causes a corresponding increase in the measured voltage. This technique allows for the measurement of vein shrinkage in relative terms. The signals from the sensing electrodes are input to a monitor, or microprocessor 32 which could send control signals to the RF generator 34 in order to control the application of RF energy to the electrodes in accordance with the relative impedance measured. Alternatively, the signals from the sensing electrodes are displayed visually on a monitor in order to allow for manual control by the physician. Measurements of the applied current and voltage applied to the electrodes can also be used to arrive at the impedance of the treatment site.

In another embodiment, the sensors 30 are temperature sensors such as thermocouples. The temperature sensors may be included on the catheter near the electrodes on the working end to monitor the temperature surrounding the electrodes and the venous section being treated. Application of RF energy from the electrodes may be halted when the monitored temperature reaches or exceeds the specific temperature at which venous tissue begins to shrink. The signals from the temperature sensors are input to the microprocessor 32 for controlling the application of RF energy to the electrodes in accordance with the monitored temperature.

Instead of sensing electrodes or thermocouples, another embodiment includes ultrasonic piezoelectric elements which emit pulsed ultrasound waves as the sensors. The piezoelectric elements are operated in a pulse-echo manner to measure the distance to the vein wall from the catheter shaft. Again, the signals representative of the pulse-echo would be input to the microprocessor 32, or to a monitor to allow for manual control, and the application of RF energy would be controlled in accordance with the distance computed between the catheter and the vein wall.

Figure 10:
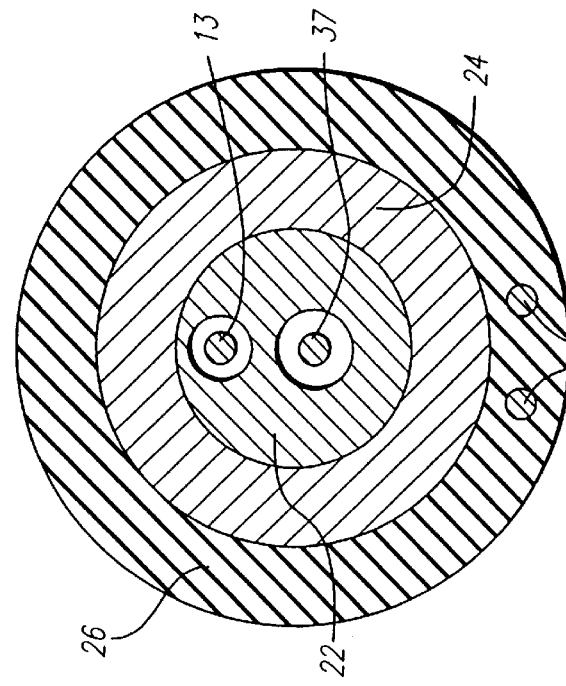
FIG. 10 is a cross-sectional view along lines 10—10 of FIG. 9.
Figure 9:
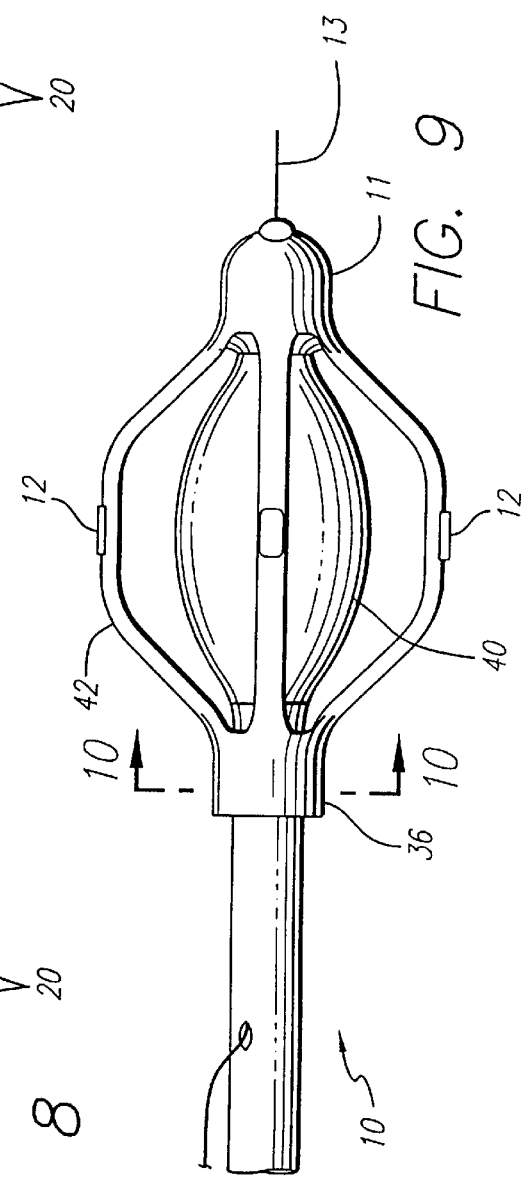
FIG. 9 is a partial side view of the working end of another embodiment of a catheter having a balloon and bendable members with electrodes in accordance with the present invention.

Another embodiment of the catheter 10, as shown in FIG. 9, includes bowable elongate members 42 having one end anchored to the working end 11 of the catheter, and the other end slidably connected to the catheter towards the connecting end. The catheter shown in FIG. 9 is similar to that shown in FIG. 3, except that instead of having the elongate members act as the electrodes themselves, the electrodes 12 are located on the elongate members 42. The elongate members 42 preferably include a flat central area for the electrodes 12. The central area remains substantially flat as the elongate members 42 are deflected and bowed outwardly. The substantially flat central area allows for a more uniform contact with the vein wall. The flat area establishes a larger surface area to assure contact between the electrode 12 on the elongate member and the vein wall. It is to be understood that the flat area need not be centrally located on the elongate member 42. The flat area should be located so as to be the first area that contacts the vein wall. The elongate members 42 at the working end of the catheter are connected to a movable tip manually controlled by a diameter actuator located at the connecting end of the catheter. The movable tip is connected to the diameter actuator by an actuation wire 37 running centrally through the catheter, as shown in FIG. 10. The diameter actuator may be threaded onto the connecting end of the catheter. Maneuvering the diameter actuator into and out of the connecting end of the catheter causes a corresponding movement in the movable tip at the working end of the catheter via the actuation wire. If the movable tip 17 is pulled toward the connecting end by the diameter actuator, then the electrodes 12 are bowed outwardly. The bowed electrodes 12 preferably expand out to treat veins having diameters of up to ten mm or more. If the movable tip 17 is pushed forward by the actuator wire 37, the electrodes 12 are then retracted towards the shaft of the catheter. Contact between the electrode and the vein wall can be maintained with the vein wall as the vein shrinks.

In one embodiment, the balloon 40 is located between the catheter shaft and the elongate members 42. Manual manipulation of a sliding sleeve or a movable tip is not required in this embodiment, and the sliding sleeve, if used, need not travel any substantial length of the catheter. The balloon 40 may be either an elastic material, such as latex, or a noncompliant material. The balloon 40 is inflated and comes into contact with the elongate members 42. As the balloon 40 is further inflated, the electrodes 12 are moved outwardly in a radial direction as the elongate members are deflected and bowed by the expanding balloon 40. The balloon is preferably inflated using a non-conductive fluid, especially where the elongate members contain the electrodes, or where the elongate member itself is conductive so as to act as the electrode. When the proper diameter for the electrodes is reached, the inflation of the balloon ceases, and the application of the RF energy begins.

The balloon 40 covers a greater surface area over the venous treatment site, and ensures proper electrode placement relative to the vein wall while controlling the amount of venous shrinkage. More precise control over the shape and diameter of the balloon is possible using the bowable members. The balloon can also be used to control the effective diameter of the catheter at the working end. As RF energy is applied, the vein begins to shrink down to the effective diameter of the catheter. The effective diameter of the catheter is reduced under the control of the physician to control the amount of shrinkage. As the effective diameter is decreased, the electrodes continue to maintain apposition with the venous tissue. The application of RF energy from the electrodes 12 is terminated after shrinking the vein to the desired diameter, which is the final effective diameter as defined by the diameter of the balloon 40 and the deflected elongate members 42. The balloon 40 is then is deflated to a minimal profile. The elongate members 42 can be fabricated from stainless steel, spring steel, or nitinol so that the elongate members 42 would be biased to return to a reduced diameter profile when the balloon is deflated.

In another embodiment, the ends of the elongate members are instead slidably located within longitudinal slots or channels disposed along the circumference of the catheter. The ends of the bowable members would slide towards the working end within these channels as the members are deflected or bowed outwardly, and retract back towards the connecting end in order to return to their original configuration.

In another alternate embodiment, the electrodes and the elongate members could be replaced by a single wire mesh or braided electrode, preferably when applying RF energy in a monopolar configuration. As before, the balloon could radially extend the mesh electrode outward into apposition with the vein wall. The balloon further controls the amount of vein shrinkage.

An alternative method for changing the effective diameter of the catheter is to move or deflect the electrodes into direct contact with the vein wall and then allow the vein wall to alter the effective diameter. As the electrodes emit RF energy, the vein wall shrinks and pushes the electrodes inwardly towards the catheter. The vein shrinkage reduces the effective diameter directly, rather than by the active control of the physician, thereby eliminating the need for constant fine mechanical adjustments to the effective diameter. A mechanism such as a push rod or fixed-diameter balloon may be included to prevent further radial contraction of the electrodes at a specific effective diameter, thereby controlling and limiting the amount of vein shrinkage. This has the advantage of maintaining the electrodes in apposition with the venous tissue so that the tissue is heated more than the surrounding blood, without requiring the physician to adjust the effective diameter of the catheter while applying the RF energy.

Other devices which are controllably expandable or extendable may be used to limit the shrinkage of the vein to a desired size. For example, a bowable conductive deflection wire may be located on one side of the catheter for achieving apposition with the vein wall. Furthermore, the non-expandable catheter shaft and electrodes, shown in FIG. 3, may be used to limit the amount of vein shrinkage during the procedure, so that the vein shrinks down to the fixed diameter of the catheter.

A balloon expandable embodiment, as shown in FIG. 11, includes the four longitudinal electrodes 12 arranged in longitudinal fashion around the circumference of the balloon 40 of the catheter 10. This embodiment is similar to the embodiments disclosed and described in connection with FIGS. 3 through 10. The particular positioning and orientation of the longitudinal electrodes is preferably equidistant so as to provide omnidirectional shrinkage and minimize lengthwise contraction of the vein. Other electrode configurations may also be employed along the balloon, including having only one pair of electrodes on one side of the balloon to focus the heating effect on that one side. The catheter 10 as shown in FIG. 11 is an over-the-wire type in which the catheter travels over the guide wire 13 through a guide wire lumen 38. A cross-section of the shaft of the catheter 10 along lines 12—12 of FIG. 11 is shown in FIG. 12. The catheter 10 further includes the braided shield 24 surrounding the guide wire lumen 38. A braid tube 54 is formed around the braid 24. The lumen 56 for the balloon 40, and the balloon tube 55, encircle the braid tube 54. The braid tube forms a sealing barrier against the inflation fluid leaking into the guide wire lumen 38 from the balloon lumen. The exterior of the catheter includes a retainer tube 57 holding the conductor leads 20, which connect the electrodes 12 to the RF generator.

In another embodiment, the electrodes 12 are located under the balloon 40 of the catheter 10. This embodiment, which is shown in FIG. 13, allows for conductive heating of the venous tissue. The catheter 10 shown in FIG. 13 is an over-the-wire type in which the catheter completely travels over the previously introduced guide wire 42. The balloon is inflated and expands to come into contact with the venous tissue. As discussed previously, the inflated balloon 40 is used to control or limit the magnitude of shrinkage of the vein to the outer diameter of the inflated balloon 40. The effective diameter is controlled by the selective inflation and deflation of the balloon 40. The inflation medium of the balloon 40 is preferably a conductive fluid, such as saline solution, so that a significant amount of the RF energy will still be transferred to the surrounding venous tissue. However, the inflation medium may absorb a certain amount of the RF energy, which will then be converted to heat. This diffusion of the RF energy could provide greater control over the shrinkage of the vein. Alternatively, a conventional heater coil or curie point element could be used in place of the electrodes 12 in order to directly heat the inflation medium, which in turn would conductively transfer the heat to the venous tissue.

An embodiment of the catheter 10, shown in FIGS. 14, 15, and 16, is capable of being deflected by a shaft deflection wire 29. By deflecting the working end of the catheter, selective apposition between the electrodes at the working end and the venous tissue at the treatment site can be maintained. The catheter includes a silver-coated copper shield 24 and an outer layer of insulation 26. The electrodes 12 may be four circumferentially spaced longitudinal electrodes, as previously discussed. FIGS. 14 and 16 only show two of four longitudinal electrodes. The catheter 10 further includes a stiffening jacket 25 formed around the catheter shaft, except for the working end of the catheter. A central hollow wire lumen 27 extends through the length of the catheter. The shaft deflection wire 29 has a stiff bend formed near its working end, and is pushed through the wire lumen 27 of the catheter. The end of the wire 29 after the stiff bend which advances through to the tip of the working end of the catheter is preferably flexible and pliant. The stiffening jacket 25 prevents the catheter shaft from being deflected by the shaft deflection wire 29 until the deflection wire reaches the working end of the catheter. The stiff bend in the deflection wire 29 moves the working end 11 of the catheter to one side. Alternatively, the deflection wire 29 is a shape-memory metal which would be relatively straight until actuated to form a bend. The electrodes 12 may then be selectively placed in apposition with the specific venous tissue to be treated. A contrast medium may also be administered to the treatment site through the lumen 27. Further, a cooling solution or fluid may be delivered to the treatment site through the lumen 27. The lumen further includes side ports 28 formed at the working end near the electrodes 12 for delivering the contrast medium and the cooling fluid. Alternatively, the lumen 27 could be closed at the tip of the working end of the catheter in order to allow an injection of contrast media or cooling solution to be forced out the side ports 28. Closing the lumen 27 at the tip further allows the deflection wire 29 to be made more stiff without concern for the stiffer wire extending past the catheter.

Another embodiment uses an asymmetrical balloon 40 to deflect the electrodes 12 at the working end 11 of the catheter to one side. The electrodes 12 are a pair of longitudinal electrodes located on one side of the catheter. As shown in FIGS. 17 and 18, the balloon 40 is located on the opposite side of the catheter. When the balloon 40 is inflated, the opposite side of the working end 11 accommodating the longitudinal electrodes is moved into apposition with the venous tissue to be treated. After treating the dilated venous section, the balloon 40 is deflated, and the catheter removed from the vasculature. It should be noted that the other mechanisms for deflecting the working end of the catheter may be used. For example, a bendable actuation wire may be used on one side of the catheter in order to perform a function similar to that of the asymmetrical balloon. The catheter further includes the jacket 26, the braid 24, and the insulation 22.

Another embodiment of the catheter 10 having electrodes 12 on the working end 11 which causes localized heating of the surrounding venous tissue and shrinkage of the vein is shown in FIG. 19. The electrodes 12 include two ring electrodes 14 and 16. The end ring electrode 14 acts as the active electrode, and the ring electrode 16 acts as the return electrode, or vice versa. The working end of the catheter includes a lumen for accepting the guide wire in an over-the rail type delivery system. The tip of the guide wire 13 is preferably rounded. The lumen is preferably insulated so as to prevent or minimize any coupling effect the RF electrodes may have on the guide wire.

The end ring electrode 14 is preferably spaced away from the tip of the working end of the catheter which may be formed from plastic or some other non-conductive material. The RF field created by the ring electrodes 14 and 16 should not extend past the end of the catheter. The inert non-conductive tip of the working end of the catheter helps prevent shrinkage past the end of the catheter by limiting the extent and formation of the RF field. This non-conductive tip acts as a shrink-limiting mandrel to prevent the veins from shrinkage to a diameter less than the catheter tip and may extend 2 to 25 mm past the electrode 14. Both electrodes 14 and 16 are preferably made from stainless steel. An insulator material 18 is located between the end electrode and the ring electrode. The catheter 10 and electrodes 12 should be constructed from materials which would allow visualization under fluoroscopy, x-ray, ultrasound, or other imaging techniques. For example, the catheter 10 may be configured to deliver x-ray contrast medium to allow visualization by fluoroscopy. Contrast media injected into the vein may be used to assess the condition of the vein and the relationship of the catheter to the treatment area of the vein by phlebography during the shrinkage process.

The catheter 10 includes a center conductor 20 surrounded by a layer of insulation 22. A silver-coated copper braid 24 surrounds the insulated center conductor, and provides flexible and torquable characteristics to the catheter shaft. A sheath 26 covers the copper braid 24. The sheath 26 is preferably made of an electrically resistive, biocompatible material with a low coefficient of friction. The center conductor 20 is connected to a power source 34 such as an RF generator, to provide RF energy to the electrodes 12.

Figure 20:
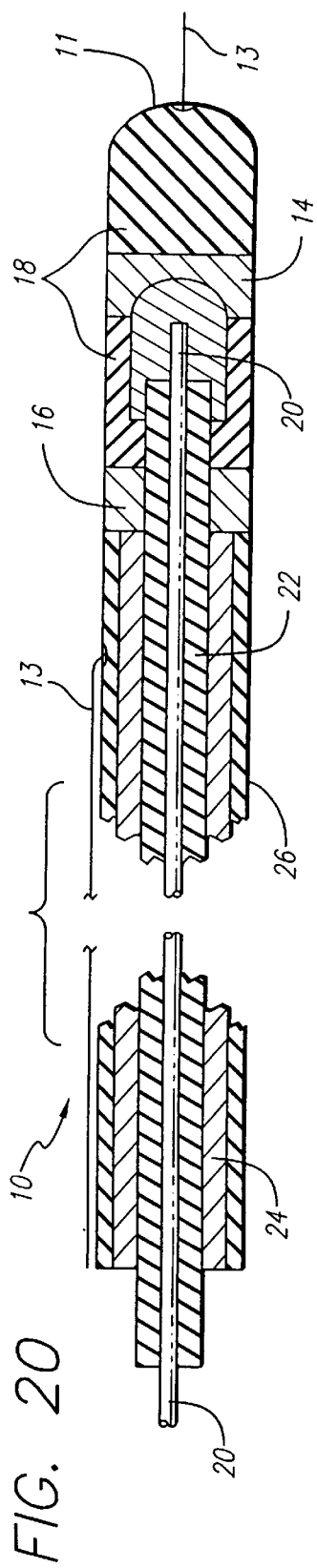
FIG. 20 is a partial cross-sectional side view of an embodiment of the catheter having a flush tip at the working end and ring electrodes for treating a dilated vein in accordance with the present invention.

The working end 11 of the catheter 10, as shown in FIG. 19, is rounded to provide an atraumatic tip. The working end 11 of the catheter 10 has an enlarged dimension which limits the amount of local vein shrinkage. An enlarged atraumatic tip may be achieved using a bulbous shape for the working end 11. Alternatively, the working end 11 and the ring electrodes 14 and 16 are flush with the shaft of the catheter as shown in FIG. 20. Different sized working ends and electrodes may be manufactured separately from the catheter 10 for later assembly with the shaft of the catheter 10 so that a single catheter shaft may be used with working ends having a variety of diameters. A working end having a specific size or shape could then be used with the catheter 10 depending on the type of vein being treated. Catheters need not be sized for the smaller veins and venules if only general shrinkage of the larger sections of the vein are to be performed to reduce the venous pressure. For example, certain larger veins have a diameter of seven to eight mm, while other veins only have a diameter of 2 to 3.5 mm. Other methods, such as monitoring the amount of shrinkage by fluoroscopy, may be used to determine and control the amount of shrinkage. In other respects, the construction of the catheter in FIG. 20 is similar to that of FIG. 19, as previously discussed.

Figure 21:
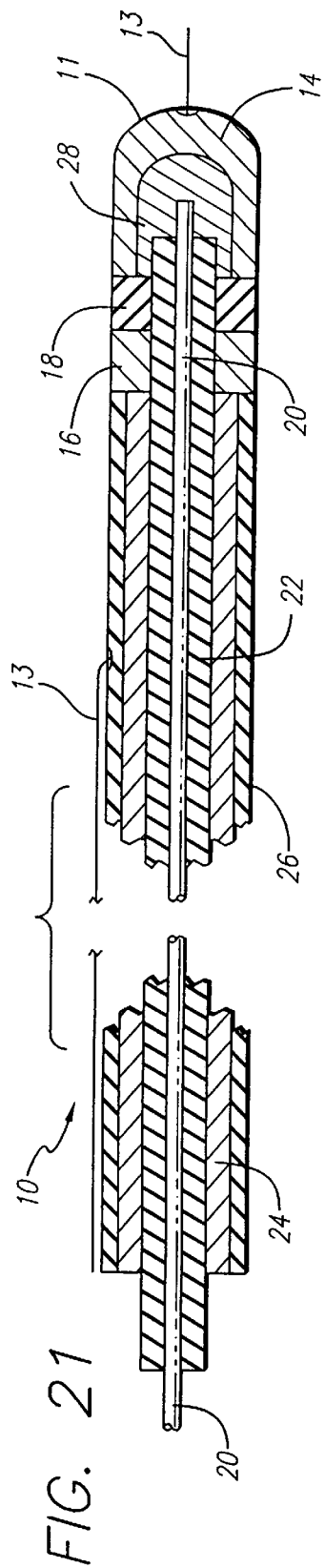
FIG. 21 is a partial cross-sectional side view of an embodiment of the catheter having a cap electrode for treating a dilated vein in accordance with the present invention.

Another embodiment of the catheter 10 includes an end electrode 14 which is a cap electrode formed on the tip of the working end 11 of the catheter 10, as shown in FIG. 21. The end electrode 14 is preferably fabricated from stainless steel. The cap electrode 14 acts as the active electrode, and the ring electrode 16 acts as the return electrode. Although described as a bipolar arrangement, the catheter may include only a single cap electrode in a monopolar arrangement. The cap electrode 14 of the catheter 10 is rounded to provide an atraumatic tip so as to minimize any damage to the surrounding venous tissue as the catheter is manipulated through the vein. The electrodes and the working end, as shown in the exemplary FIG. 21, are substantially flush with the remainder of the catheter. Alternatively, the cap electrode and the working end 11 of the catheter 10 may have an enlarged dimension from the remainder of the catheter. The braid sheath 26 covers the silver-coated, copper braid 24 of the catheter, and the sheath is flush with the outer diameter of the ring electrode 16. An insulator tube 18 is located between the end electrode and the ring electrode. At the working end of the catheter, a solder fill 28 is formed between the center conductor 20 and the end electrode 14. The center conductor 20 is isolated from the ring electrode 16 by the insulation 22. The guide wire 13 is preferably insulated from the cap electrode 14.

Figure 22:
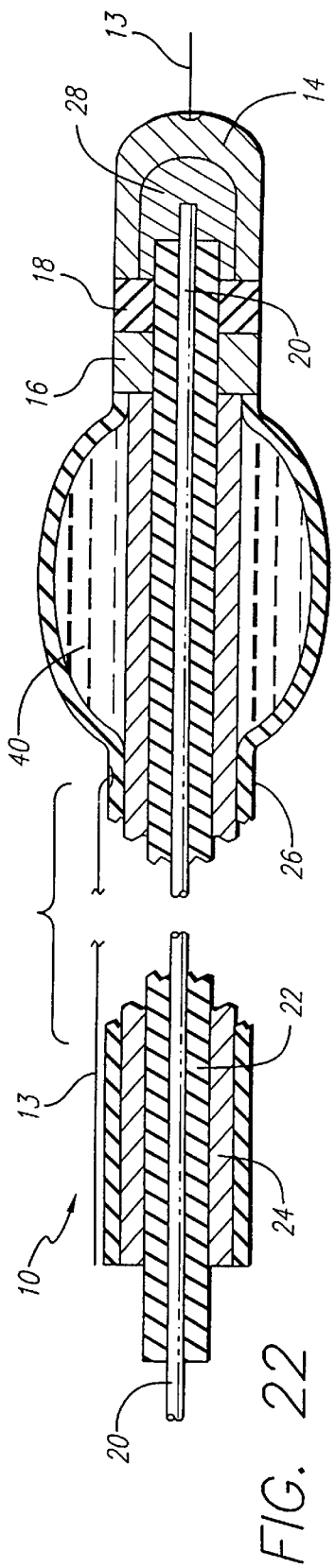
FIG. 22 is a partial cross-sectional view of another embodiment of the catheter having a cap electrode and a balloon to center the placement of the electrode within the vein to be treated.

In another embodiment, an inflatable balloon 40 coaxially placed over the braided shaft centers the catheter 10 and the electrodes 14 and 16 within the vein lumen in order to avoid unintended electrode contact with the vein lumen which could otherwise result in uneven heating of portions of the vein lumen. The balloon 40 is located adjacent to the electrode 16, as shown in FIG. 22, which is closer to the connecting end of the catheter. The balloon 40 is preferably expandable and compliant, and fabricated from an elastic material such as latex, to provide intermediate diameters. The balloon is inflated with saline, or a non-conductive solution may be used.

As can be readily ascertained from the disclosure herein, the procedure of the present invention is accomplished without the need for prolonged hospitalization or postoperative recovery. Early treatment of venous disease could prevent more serious complications such as ulceration, thrombophlebitis and thromboembolism. The cost of treatment and complications due to venous disease would be significantly reduced. Furthermore, the minimally invasive nature of the disclosed methods would allow the medical practitioner to repair or treat several venous sections in a single procedure in a relatively short period of time.

It is to be understood that the type and dimensions of the catheter and electrodes may be selected according to the size of the vein to be treated. Furthermore, although described as using RF energy from the electrode, it is to be understood that other forms of energy such as microwaves, ultrasound, direct current, circulating heated fluid, radiant light, and lasers may be used, and that the thermal energy generated from a resistive coil or curie point element may be used as well. In addition, although the present invention has been described as treating esophageal varices, the present invention may be employed to intraluminally treat varicose veins and venous insufficiency in the lower limbs, hemorrhoids, and venous-drainage-impotence of the penis.

While several particular forms of the invention have been illustrated and described, it will be apparent that various modifications may be made without departing from the scope of the invention. Accordingly, it is not intended that the invention be limited, except as by the appended claims.

We claim:

1. A method of applying energy to cause shrinkage of a dilated vein for treating esophageal varices, the method comprising the steps of:
    introducing a catheter having a working end and means for heating located at the working end, to a treatment site in a vein;
    positioning the means for heating at the treatment site in the vein;
    applying energy from the means for heating to heat the treatment site and cause shrinkage of the vein;
    terminating the emission of energy from the means for heating after sufficient shrinkage of the vein so as to reduce vein dilation and so that the vein remains patent.

2. The method of claim 1, wherein the step of introducing the catheter includes the step of advancing the catheter through the superior mesenteric vein to the portal vein branches.

3. The method of claim 1, wherein the step of positioning the means for heating at the treatment site further includes the step of placing the means for heating at the treatment site to shrink the portal vein branches leading to the esophagus so as to reduce the esophageal venous wall stress from the portal venous system.

4. The method of claim 1, wherein the step of positioning the means for heating further includes the step of arranging the means for heating for achieving circumferential shrinkage of the vein.

5. The method of claim 1, wherein the step of positioning the means for heating further includes the step of moving the means for heating into apposition with the vein wall at the treatment site.

6. The method of claim 1, wherein the step of positioning further includes the step of increasing an effective diameter of the catheter to place the means for heating into apposition with the vein wall; and the step of applying energy further includes the step of reducing the effective diameter of the catheter so as to maintain apposition with the vein wall as the vein wall shrinks.

7. The method of claim 1, wherein the step of applying energy further includes the step of limiting the shrinkage of the vein to a selected diameter.

8. The method of claim 1, wherein the step of applying energy further includes the step of controlling the energy from the means for heating so as to minimize coagulation in the vein.

9. The method of claim 1, wherein the step of applying energy further includes the step of controlling the energy from the means for heating so as to control the spread of heating at the treatment site of the vein.

10. The method of claim 1, wherein the step of applying energy further includes the step of applying energy in a directional manner so as to cause preferential heating of the vein.

11. The method of claim 1, further comprising the step of determining the extent of shrinkage of the vein using fluoroscopy.

12. A method of applying energy to cause the shrinkage of a dilated vein for treating esophageal varices, the method comprising the steps of:
    introducing a catheter having a working end and at least one electrode located at the working end, to a treatment site in the vein;
    positioning the electrode at the treatment site in the vein;
    applying radio frequency energy from the electrode to heat the treatment site and cause shrinkage of the vein;
    terminating the step of applying radio frequency energy from the electrode after sufficient shrinkage of the vein so as to reduce the esophageal varices while the vein remains patent.

13. The method of claim 12, wherein the step of introducing the catheter includes the step of advancing the catheter through the superior mesenteric vein to the portal vein branches.

14. The method of claim 12, wherein the step of positioning the means for heating at the treatment site further includes the step of placing the electrode at the treatment site to shrink the portal vein branches leading to the esophagus so as to reduce esophageal venous wall stress from the portal venous system.

15. The method of claim 12, wherein the step of positioning the electrode further includes the step of arranging a plurality of electrodes on the catheter for achieving circumferential shrinkage of the vein.

16. The method of claim 12, wherein the step of positioning further comprises the step of inflating a balloon with an inflation medium so that the balloon engages the vein; wherein the step of applying energy further includes the step of heating the inflation medium by the heating means, wherein the treatment site is heated by the conduction of heat from the balloon.

17. The method of claim 12, wherein the step of positioning the electrode further includes the step of moving the electrode into apposition with the vein wall at the treatment site.

18. The method of claim 12, wherein the step of positioning further includes the step of deflecting an elongate member at the working end of the catheter to place the electrode in apposition with the vein wall at the treatment site.

19. The method of claim 12, wherein the step of positioning further includes the step of inflating a balloon on the catheter to engage an elongate member, wherein the elongate member is deflected to place the electrode in apposition with the vein wall at the treatment site.

20. The method of claim 12, wherein the step of positioning the electrode at the treatment site further includes the step of inflating a balloon on the catheter to move the electrode into apposition with the vein wall.

21. The method of claim 12, wherein the step of positioning further includes the step of moving a deflection wire through the catheter to deflect the catheter and the electrode to one side of the vein at the treatment site.

22. The method of claim 12, wherein the step of positioning further includes the step of actuating a deflection wire on one side of the catheter so as to move the catheter and the electrode on the side of the catheter opposite the deflection wire to one side of the vein.

23. The method of claim 12, wherein the step of positioning further includes the step of inflating a balloon on one side of the catheter so as to move the catheter and the electrode on the other side of the catheter to one side of the vein at the treatment site.

24. The method of claim 12, wherein the step of positioning further includes the step of inflating a balloon on the catheter to center the catheter and the electrode within the vein.

25. The method of claim 12, wherein the step of applying energy further includes the step of limiting the shrinkage of the vein to a selected diameter.

26. The method of claim 12, wherein the step of applying energy further includes the step of limiting the shrinkage of the vein by inflating a balloon to a selected diameter; wherein the inflated balloon prevents shrinkage of the vein beyond the selected diameter.

27. The method of claim 12, wherein the step of positioning the electrode further includes the step of placing the electrode into apposition with the vein wall; and the step of applying energy further includes the step of reducing an effective diameter of the catheter in a controlled manner so as to maintain apposition with the vein wall as the vein wall shrinks until a diameter for the vein is achieved, wherein the vein continues to function.

28. The method of claim 12, wherein the step of positioning the electrode further includes the step of placing the electrode into apposition with the vein by increasing an effective diameter of the catheter, wherein the shrinkage of the vein reduces the effective diameter of the catheter; and the step of limiting the shrinkage of the vein further includes the step of preventing the effective diameter of the catheter from being reduced to less than a selected diameter representing the sufficient shrinkage of the vein.

29. The method of claim 12, wherein the step of applying energy further includes the step of limiting the shrinkage of the vein to the fixed diameter of the catheter at the working end.

30. The method of claim 12, wherein the electrode includes a plurality of longitudinal electrodes, and the step of applying the high frequency energy further includes the step of providing the high frequency energy to the longitudinal electrodes along the circumference of the working end of the catheter; wherein the vein is shrunk circumferentially and axial shrinkage of the vein is minimized.

31. The method of claim 12, wherein the electrode is a ring electrode, and the step of applying the high frequency energy further includes the step of providing the high frequency energy to the ring electrode at the working end of the catheter.

32. The method of claim 12, wherein the step of applying the high frequency energy further includes the step of providing an inert tip at the working end of the catheter past the electrode to prevent vein shrinkage past the working end of the catheter.

33. The method of claim 12, further comprising the step of delivering a cooling fluid to the treatment site for preventing thermal coagulation.

34. The method of claim 12, wherein the step of applying energy further includes the step of applying energy in a directional manner so as to cause preferential heating of the vein.

35. The method of claim 12, further comprising the step of determining the extent of shrinkage of the vein.

36. The method of claim 12, further comprising the step of determining the extent of shrinkage of the vein using fluoroscopy.

37. The method of claim 12, further comprising the step of determining the extent of shrinkage of the vein using ultrasound imaging.

38. The method of claim 12, further comprising the step of determining when to terminate the applying of radio frequency energy by measuring the time at which a specific temperature has been achieved at the treatment site.

39. A method of applying energy to cause the shrinkage of a dilated vein for treating esophageal varices, the method comprising the steps of:

introducing a catheter having a working end and at least one electrode located at the working end, to a treatment site in the vein;

positioning the electrode at the treatment site in the vein;

applying energy from the electrode to heat the treatment site and cause shrinkage of the vein;

delivering a fluid to the treatment site in the vein;

terminating the applying of radio frequency energy from the electrode after sufficient shrinkage of the vein so that the vein remains patent.

40. The method of claim 39, wherein the step of positioning the electrode further includes the step of placing the electrode into apposition with the vein wall; and the step of applying energy further includes the step of reducing an effective diameter of the catheter in a controlled manner so as to maintain apposition with the vein wall as the vein wall shrinks until a diameter for the vein is achieved, wherein the vein continues to function.

41. The method of claim 39, wherein the step of positioning the electrode further includes the step of placing the electrode into apposition with the vein by increasing an effective diameter of the catheter, wherein the shrinkage of the vein reduces the effective diameter of the catheter; and the step of limiting the shrinkage of the vein further includes the step of preventing the effective diameter of the catheter from being reduced to less than a selected diameter representing the sufficient shrinkage of the vein.

* * * * *

UNITED STATES PATENT AND TRADEMARK OFFICE
CERTIFICATE OF CORRECTION

PATENT NO. : 6,033,397
DATED : March 7, 2000
INVENTOR(S) : Michael D. Laufer, Brian E. Farley.

It is certified that error appears in the above-identified patent and that said Letters Patent is hereby corrected as shown below:

Column 11, line 14, change "39", to read --38--.

Signed and Sealed this

Twenty-seventh Day of February, 2001

*Attest:*

NICHOLAS P. GODICI

*Attesting Officer*　　*Acting Director of the United States Patent and Trademark Office*